(12) United States Patent
Tester et al.

(10) Patent No.: US 6,649,191 B1
(45) Date of Patent: Nov. 18, 2003

(54) ORALLY ADMINISTRABLE COMPOSITIONS COMPRISING CATION CROSS-LINKED POLYSACCHARIDE AND A POLYMER DIGESTIBLE IN THE LOWER GASTROINTESTINAL TRACT

(75) Inventors: Richard Frank Tester, Glasgow (GB); John Karkalas, Glasgow (GB)

(73) Assignee: Glycologic Limited, Glasglow (GB)

( * ) Notice: Subject to any disclaimer, the term of this patent is extended or adjusted under 35 U.S.C. 154(b) by 0 days.

(21) Appl. No.: 09/673,901

(22) PCT Filed: Apr. 22, 1999

(86) PCT No.: PCT/GB99/01240

§ 371 (c)(1),
(2), (4) Date: Oct. 20, 2000

(87) PCT Pub. No.: WO99/53902

PCT Pub. Date: Oct. 28, 1999

(30) Foreign Application Priority Data

Apr. 20, 1998 (GB) .............................................. 9806595
May 15, 1998 (GB) .............................................. 9810375

(51) Int. Cl.$^7$ ................................................ A61K 9/16
(52) U.S. Cl. ...................... 424/488; 424/400; 424/439; 424/485; 424/489; 514/778; 514/779; 514/782; 514/944
(58) Field of Search ................................ 424/484, 485, 424/486, 487, 488, 439, 489

(56) References Cited

U.S. PATENT DOCUMENTS 5,840,332 A * 11/1998 Lerner et al. ................ 424/464
5,972,399 A * 10/1999 Lapre et al. ................. 426/302

FOREIGN PATENT DOCUMENTS

EP       0 243 930 A1       11/1987

OTHER PUBLICATIONS

Ishmael Joseph et al., "Indomethacin sustained release from alginate–gelatin or pectin–gelatin coacervates", Interntl Journal of Pharmaceutics, vol. 126, 1995, pp. 161–168.

* cited by examiner

Primary Examiner—James M. Spear
(74) Attorney, Agent, or Firm—Drinker Biddle & Reath LLP

(57) ABSTRACT

Orally administrable compositions comprising cation cross-linked polysaccharides are provided. The compositions have the ability to mask the taste and delay the release of an active material included therein. A novel method for the preparation of the compositions is also provided. The cation cross-linked polysaccharide is preferably selected from alginic acid and demethylated pectin and the composition further comprises a digestible polymer, preferably chosen from starch, starch derivatives, α-glucans, peptides and polypeptides.

13 Claims, 18 Drawing Sheets

ORALLY ADMINISTRABLE COMPOSITIONS COMPRISING CATION CROSS-LINKED POLYSACCHARIDE AND A POLYMER DIGESTIBLE IN THE LOWER GASTROINTESTINAL TRACT

This application is the U.S. national phase application of PCT International Application No. PCT/GB99/01240 Apr. 22, 1999.

The present invention is concerned with compositions for oral administration which have the ability to mask the taste of an active ingredient contained therein as well as methods for the preparation of such compositions and their use in the administration of a wide variety of active ingredients. The invention is also concerned with the same compositions which control the rate of release of active ingredient contained therein.

Oral dosage forms provide a convenient vehicle through which one or more pharmaceutically active ingredients may be administered to a patient requiring therapy. A wide variety of dosage forms exist and the choice of any particular form depends upon individual requirements. Dosage forms may be prepared by granulating one or more active ingredients with a carrier or excipient to give a mixture that is suitable for further processing. Tablets are typically prepared by compressing the granulated mixture in a die, granules are prepared by extruding and optionally spheronising the mixture and capsules are prepared by filling a capsule shell with pre-prepared tablets or granules. Typical excipients include synthetic materials such as polyvinylpyrrlidone and co polymers of methacrylic acids is as well as natural polymers such as cellulose, starch and alginic acid.

Dosage forms produced in this way comprise particles of active ingredient and excipient which are packed together rather like balls in a box, so that when the form erodes discrete particles of active ingredient are exposed and then lost to the surrounding environment through dissolution. The rate at which the individual particles diffuse into the surrounding environments depends, in part, upon their size. Smaller particles having a larger surface area to volume ratio dissolve more rapidly than larger particles. Erosion of the dosage forms occurs upon ingestion causing the active material to be released to the surrounding environment. Unless such dosage forms are coated it may be possible to taste the active ingredient. Such dosage forms are unable to delay release of the active material.

A patient who is able to taste an active ingredient upon ingestion of the dosage form may be reluctant or even refuse to comply with the therapeutic regime imposed. The problem is particularly acute with both the elderly and very young who have trouble swallowing tablets. Taste masking is a recognised problem and has been discussed in an article entitled "Taste-masking of Oral Formulations" by Galanchi & Ghanta in Pharmaceutical Manufacturing Limited, 1996, Sterling Publications Ltd.

The therapeutic management of patients with phenylketonuria, for example, requires the administration at regular periods throughout the day of an amino acid protein substitute that excludes phenylalanine in order to maintain the plasma phenylalanine levels within an acceptable range. The protein substitutes are usually administered prior to mealtimes in the form of a drink, which is highly flavoured to mask the bad taste of the amino acids. Dissolution of the active material starts upon administration. Although this regime allows the phenylalanine levels to be adequately maintained within specified levels during the day, the impracticality of administering the protein substitute during the hours in which the patient is asleep means that it is not possible to maintain the olasma phenylalanine concentration at a constant level over a 24-hour period. This presents major problem with regards the therapeutic management of such patients.

It is well known to provide dosage forms with sugar coatings to mask the flavour of an unpleasant tasting active ingredient. However, the problem with this is that unless the dosage form is swallowed immediately the sugar coat rapidly dissolves and exposes the active material to the buccal environment, which leaves an unpleasant taste. These dosage forms are also unable to delay the release of an active material contained therein.

The problem of providing dosage forms with the ability to mask taste has been addressed in WO 93/01805. This disclosed rapidly disintegrating multiparticulate tablets prepared by granulating ethylcellulose or polymethacrylic acid coated crystals or granules of active material with excipients and flavouring and compressing the resulting mixture to form a tablet. This preparation requires a large number of processing steps, making these tablets both complicated and expensive to prepare.

Tablets coated with layers of alginic acid and calcium gluconate were found to mask the taste of the tableted active material for a limited period of time due to the formation of a gel upon ingestion of the dosage form (Kaneko et al, Chem. Pharm. Bull. 45(6), 1063–1068 (1997)). An outer coat of calcium gluconate gave a masking time of 1 minute, whereas an outer coat of alginate gave a masking time of between 0.5 and 3 minutes; the masking time was found to be dependent upon the relevant thickness of the alginate and gluconate coats. These tablets are suitable for administration if the residence time in the mouth is relatively short, but may cause problems if the patient is unable to swallow tablets, requires a dispersible dosage form or has a tendency to regurgitate any food ingested.

Alginic acid is a naturally derived polysaccharide formed from polymers of D-mannuronic acid and L-guluronic acid. Its use as a pharmaceutical excipient is well known (EP 0 213 083 and GT Colegrave, Proc. Intern. Symp. Control Rel. Bioact. Mat; 19 (1992) 271–272). Other naturally occurring polysaccharides include starch, cellulose, pectins and chitosans. None of these naturally occurring polysaccharides except starch are broken down by the human digestive enzymes in the small intestine although all are susceptible to microbiological attack by the microorganisms or flora inhabiting the large intestine of the digestive tract.

Alginic acid contains at least three different types of polymer segments: poly($\beta$-D-mannopyransosyluronic acid) segments, poly($\alpha$-L-gulopyranosyluronic acid) segments and segments with alternating sugar units. The ratios of the constituent monomers and the nature of the chain segments vary with the source and determine the specific properties of the polysaccharide. A useful property of alginates is their ability to form gels by reactions with cations, especially divalent cations such as calcium ions. The type of gel formed depends on the source of alginic acid. Alginates with a higher percentage of polyguluronate segments from more rigid, brittle gels whereas alginates with a higher percentage of polyguluronate segments or more elastic, deformable gels. The rate of gel formation as well as the quality and texture of the resultant gel can be controlled by the solubility and availability of the cation source.

The ability of alginic acid to form gels has been used in the preparation of a variety of dosage forms (Ostberg et al, International Journal of Pharmaceutics, 112 (1994) 241–248 and Ostberg et al, Acta Pharm. Nord. 4(4), 201–208 (1992)).

Formulations containing theophylline, a relatively soluble drug, have been prepared by extruding a suspension of theophylline, in alginic acid solution into a theophylline-saturated solution of calcium chloride. The granules formed were found to be unsuitable for use as a controlled release formulations due to the high rate of release of active material in acidic media.

A further problem with formulations prepared according to the method of Ostberg is that upon formulation of the alginic acid drug suspension and extrusion of that suspension into calcium chloride solution, some of the particulate matter dissolves in the alginic acid solution and recrystallises at the surface of the microspheres upon drying. This means that using the methods of Ostberg it is neither possible to produce microspheres comprising particles or crystals of predefined size due to the soluablilisation thereof, nor is it possible to obtain microspheres having the active material homogeneously distributed throughout due to recrystallisation at the surface. Inhomogeneities in the structure of the microsphere means that sustained or controlled release of the active material from the matrix will be difficult or impossible to achieve, whereas changes in the crystal size within the matrix will influence the rate of dissolution of the active material from the matrix. These all represent significant problems in the field of drug release.

Alginic acid gels and those formed by interpenetrating network of alginic acid and polyacrylic acid have also been used for the preparation of controlled release formulations containing fat soluble drugs (Yuk et al, J. Controlled Release 37 (1995) 69–74). Solutions of alginic acid, optionally containing polyacrylic acid, were used to form an oil in water emulsion including an active material. This emulsion was extruded into a solution of calcium chloride to give a gel having oil encased active material distributed therein. A problem with these formulations is that although the oil droplets are homogenously distributed throughout the gels initially formed the hydrophobic and hydrophillic phases tend to separate upon drying so that the solid matrix is no longer homogeneous. The controlled release nature of these devices is thought to be a result of their ability to swell in response to pH changes occurring during their passage through gastro-intestinal (GI) system. Although these controlled or delayed releases profiles are readily obtainable under normal conditions they may not be released if there is any disturbance in the acidity or alkalinity of the GI tract.

The maximum drug loading achievable using the system was only 15%. The inability to achieve drug-loading levels in excess of this represents a particular problem of administration. In order to achieve a predetermined therapeutic level either large amounts of the dosage form will be required, or the frequency of administration will need to be increased; in each case patient compliance will be affected.

Microspheres containing water-soluble drugs as β-lactam antibiotics have been prepared by the addition of a calcium chloride solution to water in oil emulsion of alginate and drug in isoctane (Chun et al, Arch. Pharm. Res., 19(2) 106–116 (1996)). The amount of drug present in the final formulation was less than 10%. When the amount of drug exceeded 5% the distribution of active material within the matrix deviates from homogeneity as drug crystals appeared on the surface of the microspheres. This affects the ability of the dosage form to provide sustained or controlled release of the active material therefrom. Their ability to mask the taste of an active material included therein is also compromised.

Native Starch is synthesised in the form of roughly spherical granules ranging in diameter from approximately 1 to 100 μm. Native starch granules contain polysaccharide (α-glucan, c. 83–90%), water (c. 10–17%), lipid (cereal starches only as free fatty acids and lysophospholipids, c. 0–1.5%) and protein (<0.5%). The polysaccharide comprises amylose (an essentially linear α-(1–4)-glucan with a molecular weight of about 0.5 million) and amylopectin (with a molecular weight of a few million, containing c. 95% α-(1–4)- and c. 5% α-(1–6)-bonds). Native starches are semi-crystalline because external chains of amylopectin form double helices that are packed together in crystalline regions. These regions form alternating shells with amorphous regions radiating from the centre (hilum) to periphery of starch granules.

The amylose to amylopectin ratio in starches has a marked effect on properties. Starches with <5% amylose (>95% amylopectin) are described as waxy, c. 30% amylose (70% amylopectin) as normal and >40% amylose (<60% amylopectin) as high amylose or amylo-starches. The size and branching patterns of the amylose and amylopectin molecules vary between botanical species and are hence under genetic control. The structures are subject to modification by plant breeding, mutagens and transgenic technology.

To solubilise starch, it must be gelatinised by heating in excess water above a temperature (typically 80° C.) which associates the double helices and crystallites. The gelatinisation properties of starch are specific properties controlled by genetic and environmental factors. A concentration of c. 2% solubilised starch is a viscous fluid, c. 4% a gel.

Starch can form physical entrapments of other molecules when dried. The aniylose (and some suggest the external chains of amylopectin) molecules may form helical inclusion complexes with guest molecules (like fatty acids). These resemble springs where the spring is the polysaccharide with the guest molecules in the central core. Upon retrogradation (as in the staling of bread), the polysaccharide chains may also form double helices with time. These double helices contribute to the 'resistant starch' fraction of foods.

Alginic acids may be purchased as the insoluble acid or salts (e.g. sodium salts). They vary in size and ratio of the constituent sugars (mannuronic and guluronic acids). If the salts are dissolved in water, they can be gelled by the addition of multivalent cations like calcium and zinc. The cations crosslink the acid groups and cause gellation.

Pectins—especially the demethlyated forms which are essentially polygalacturonic acid—can also gel with cations as described above for the alginates.

It is very hard to form discrete forms of dried starch gels and hence discrete molecular entrapment systems, because the gelatinised starch gels (>4% solubilised polysaccharide) distort upon drying. However, oven drying can make quite rigid gels that can include retrograded material and inclusion complexes.

Although dissolved alginic acids/alginic acid salts and pectins/pectin salts can cold gel in the presence of cations, the gels end to be quite easily disrupted if the cations are discharge as in for example acid solution. Physical matrices of starches—especially those containing helical inclusion complexes and retrograded materials—do, on the other hand, resist dispersion in acids.

Japanese Patent document 6-100602 concerns taste-masking using granulated pregelatinised starch. Although cellulose has been added, a cation driven gelling agent such as sodium alginate or pectin is not envisaged.

Japanese patent document 9-208495 concerns extruding a drug with a mix including alginic acid and hydroxypropylcellulose, drying and then spraying with calcium lactate to coagulate. Taste masking is apparent. Although hydroxypropylcellulose has been added, a cation driven gelling agent such as sodium alginate or pectin is not envisaged. No starch is envisaged.

There is therefore a need for dosage forms with the ability to solve the above mentioned problems. The present invention addresses at least some of those needs.

A first aspect of the present invention provides the use of an orally administrable, solid, erodible composition comprising a divalent or multivalent cation cross-linked polysaccharide for masking the taste of an active material entangled therein. The polysaccharide used gels in the presence of a divalent or multivalent cation to form a polymeric matrix having cation cross-linked polymer molecules. Dosage forms prepared using these polysaccharides which further comprise an active material are substantially homogeneous in nature. By homogeneous it is to be understood that the active material is uniformly distributed throughout the polysaccharide matrix. The homogeneity of the dosage forms can be determined using techniques such as scanning and transmission electron microscopy (SEM and TEM). By entangled it is to be understood that any active material is immobilised within and/or retained by the interpenetrating mesh formed by the polymer strands comprising the matrix form.

Dosage forms produced from these compositions have been found to have a remarkable ability to mask the taste of unpleasant tasting active materials such as ibuprofen and amino acids for prolonged periods of time after administration. The dosage forms may be produced in any suitable form but are preferably in the form of microspheres. By masking it is to be understood that the receptors on the tongue are shielded from the active material through entrapment by the polysaccharide and consequently the active material cannot be tasted. The dosage forms also have a good mouthfeel, the oral sensation being smooth or creamy rather than granular or gritty and may be mixed into a paste with a carrier liquid ready for subsequent administration. These compositions are also able to retain a large amount of drug and drug loadings in the excess of 80% having been achieved. The taste masking of compositions having a drug loading of between 40 and 95% of an active material, preferably between 45 and 85% and especially between 60 and 75% have been achieved. The ability to mask taste as well as achieve a high drug loading provides many advantages such as the simplification of the therapeutic regime.

Using the compositions of the invention it is also possible to readily control the particle or crystal size of the active material entangled within the polymeric matrix. In this way the compositions may be used to further control the release of the active material from the matrix; the dissolution rate of an active material from compositions containing smaller crystals is generally greater than from compositions containing larger crystals. The size of the particles that can be retained within the dosage form can be readily determined using SEM and TEM and varies from about 1 $\mu$m to 100 $\mu$m and is limited by the size of the dosage form. Dosage forms containing particles outside these size ranges are also envisaged in appropriate circumstances.

The compositions according to the first aspect of the invention have been found to substantially resist attack by acid (comparable to the acidic environment of the stomach); they are, however, susceptible to attack by the micro-organisms found in the colon. These compositions therefore exhibit properties that render them suitable for the delivery of an active material to the small intestine and perhaps beyond.

Solutions of polysaccharide that are suitable for the preparation of the compositions of the present invention are those which are able to gel as a consequence of cross-linking with a divalent or multivalent cation at room temperature. Solutions containing one or more polysaccharides such as alginic acid and (demethylated) pectins have been found to be suitable for this purpose. Particularly good results have been achieved with alginic acid and in a first preferred embodiment of the first aspect of the invention the polysaccharide used is alginic acid.

Any suitable alginic acid or salt thereof may be used; this may be in derivatised or non-derivatised form. Alginic acids or their salts having a molecular weight in the range 48,000 to 186,000 are preferred. It is recognised that alginic acid is insoluble and salts such as sodium slats are preferred. Alginic acid may be used alone, or it may be present as a mixture with another polysaccharide that gels in presence of a divalent or multivalent cation, such as pectin. It will be appreciated that the nature of the alginic acid or alginic acid salts employed will affect the type of gel obtained. If a harder, more brittle gel is required, alginic acids having a higher proportion of guluronic acid should be used. Alginic acids containing a higher proportion of mannuronic acid give rise to softer, more malleable gels. Alginic acids having a ratio of guluronic to mannuronic acid in the range 70:30 to 20:80, especially 40:60 are suitable for the present application. In addition the alginic acids used may contain between 18 and 69% of poly($\beta$-D-mannopyranosyluronic acid) segments; between 15 and 58% of poly($\alpha$-L-gulopyranosyluronic acid) segments and between 16 and 40% of segments with alternating sugar units.

If pectins are used these may be selected from, for example, one or more of polygalacturonic acid and de-esterified or partially de-esterified pectins or derivatives thereof. Polygalacturonic acid is an essentially linear molecule. Pectins having a molecular weight in the range 10,000 to 70,000, preferably 20,000 to 60,000 and especially 25,000 to 50,000 may be used. As with the alginic acid, the pectins may be used lone or in combination with other polysaccharides that gel in the presence of a divalent or multivalent cation.

Any physiologically tolerable divalent or multivalent cation may be used to cross-link the polymer molecules. Suitable cations include calcium, zinc, copper and iron. Preferably the cation is calcium. The solubility of a cation source is known to influence the rate of gel formation; gel formation is slower with less soluble cation sources. It will be appreciated that the rate of gel formation will be dependent upon the choice of cation source. Suitable sources of calcium, for example include salts of calcium with chloride, acetate, carbonate, sulphate, tartrate and gluconate.

In order to modify the release characteristics of the compositions, facilitate their further processing or contribute to the sensory characteristics, it may be necessary to add additional ingredients. Typical additives include flavourings, disintegrants, digestion facilitators and digestion inhibitors. Such additives are well known to a person skilled in the art. Additives that promote disintegration include cellulose polymers such as carboxymethylcellulose, hydroxyethylcellulose, hydroxypropylcellulose, methylcellulose, sodium carboxymethylcellulose, galactomarinose, kaolin, bentonite and talc. Hydrophobic additives tend to retard disintegration. Examples of hydrophobic additives include polyethylene, polyvinylchloride, methacrylate-methacrylate co-polymer, fatty acid esters, triglycerides and carnauba wax.

It is also possible to use compositions according to the first aspect of the invention in which the solid, erodible composition further comprises a digestible polymer choosen from the group comprising starch, starch derivatives and α-glucans, (hereinafter referred to as the "starch-type polymer"). By the addition of a digestible starch-type polymer the release characteristics of the composition may be mcodified. Mixtures of digestible polymers may be used. The digestible starch-type polymer does not form a gel in the presence of a divalent or multivalent cation. By digestible it is to be understood that the polymer is resistant to the acidic environment of the stomach but is susceptible to attack by the enzymes and/or micro-organisms or fauna present lower gastro-intestinal tract. The addition of a starch-type polymer makes it possible to more accurately target the site of release on an active material from the compositions within the GI tract. For example, by employing a polymer that is resistant to the acidic environment of the stomach but is digested by the amylase enzymes of the ileum, it is possible to effect drug release in the small intestine.

However, if the starch-type polymer is predominantly digested by the microorganisms present in the colon, it is possible to affect colonic release. Such compositions may be used as oral controlled or delayed release compositions.

An embodiment of the invention therefore provides the use of a composition which further comprises a digestible, starch-type polymer which, together with the first polysaccharide, forms an interpenetrating polymer network which gels in the presence of a divalent or multivalent cation to form a cation cross-linked polymeric matrix for masking the taste of an active material entangled therein. Active materials introduced before gelling become entangled in the polymer network upon gelling. Upon drying a substantially homogeneously solid matrix composition is formed having the active material uniformly distributed throughout the matrix.

These compositions also have superior taste-masking properties. They are able to mask the taste of a large range of both water-soluble and fat-soluble active ingredients. Typical ingredients the taste of which may require masking include amino acids such as those administered to patients suffering from phenylketonuria, theophylline, proteins, enzymes, carbohydrates, lipids, vitamins and minerals, analgesics such as aspirin, non-steroidal anti-inflammatory drugs such as ibuprofen, antihistamines such as diphenylhydramine, decongestants, expectorants, $H_2$ antagonists and antitussives.

Using the compositions of the invention it is also possible to control the crystal or particle size of the active material substantially homogeneously distributed throughout the matrix structure. If desired, active material having a range of predetermined particle or crystal sizes may be present in the compositions according to the invention. This makes it easier to control the rate of dissolution of the active material from the matrix: dissolution from matrices containing larger crystals or particles of drug or active material tends to be slower than from matrices containing smaller crystals or particles.

Starch and derivatives can form strong physical matrices after drying starch solutions and gels. Also, when α-glucans dry they can form rigid matrices because double helices are formed (as occurs during retrogradation or staling). Also, the amylose fraction in particular can form single helices (like springs) containing guest molecules (drugs). However, alginate forms gels easily in the cold in the presence of cations. Hence, the alginate-starch or pectin-starch is symbiotic. The non-starch polysaccharides readily gel but the starch-type polymer imparts unique entrapment and digestibility characteristics.

The compositions are particularly suitable for the treatment of phenylketonuria; in addition to their being pleasant and easy to administer, they are also able to delay the release of the active agent for a period of time in and after the composition has left the stomach. This makes it possible to maintain the patient's phenylalanine plasma levels within a predetermined range over a 24 hour period.

The compositions of the invention may also be used in the preparation of dosage forms that comprise bacteria as the active material. Bacteria contained within the polymer matrices of the invention have been found to retain their viability and are not substantially affected by entanglement with the dosage form. An example of a bacterial genus, which may be successfully including within the dosage forms according to the invention, is Lactobacilli. Such bacteria are normally destroyed by the acidic environment of the stomach and cannot, therefore, be delivered intact to areas of the GI tract such as the colon. It will therefore be appreciated that by including bacteria in the compositions of the invention it is possibly to effectively by-pass the effects of the stomach and deliver bacteria to regions of the GI tract such as the colon.

Without wishing to limit the scope of the invention it is believed that the starch-type polymer has the ability to reinforce the polymer network and increase the extent of cross-linking therein. When the starch-type polymer contains groups such as phosphate, carboxylate or sulphate, the cross-linking cations are able to bind to these groups in addition to the carboxylate groups of the alginic acid. This increases the extent of cross-linking within the polymer network. The formations of an interpenetrating network also contributes to increasing the resistance of the composition to the acidic conditions of the stomach; it is believed that the active material becomes entangled within thy polymer network and is more firmly retained within the matrix.

Preferred starch-type, digestible polymers include polysaccharides such as starch or any suitable α-glucan or derivadive thereof. The use of starch is especially preferred. Solutions of gelatinised starch having a concentration in excess of 5% by weight form rigid gels on cooling. However, the presence of divalent or multivalent ions is not necessary to affect gelation of the starch solutions. Although starches readily gel post gelatinisation, they are difficult to form. Alginic/pectin on the other hand is relatively easy because of the cation driven gelation. Hence there is a symbiotic effect of using a combination. Derivatised, mutant, hydrolysed and chemically, enzymatically or genetically modified starches may be used. These may be in gelatinised or partially gelatinised form. The properties of these types of starch and the procedures used to verify their characteristics are taught in patent application No Wo 97/34932, which is incorporated herein by reference. This also teaches the factors to be taken into account in selecting a form of starch having a particular digestibility characteristic.

The digestibility characteristics of the starch depend upon its source, composition and extent of modification—especially gelatinisation. Crystalline starch is resistant to acid and amylase hydrolysis. The crystallinity may be native crystallinity (where exterior chains of amylopectin complex, pack together and form concentric repeating shells of these double helices) or as a consequence of retrogradation (amylose and amylopectin) and complexing (especially amylose) during post processing. Amorphous material is always more susceptible to hydrolysis. Crystalline material is also more resistant to fermentation by micro-organisms than is amorphous material. The release of active material will therefore be delayed relative to material containing a larger proportion of crystalline starch material.

The starches used may contain between 0 and 100% of amylose and between 100 and 0% of amylopectin respectively. The choice of starch may be influenced by the nature of the desired release. The amylose fraction of the starch may have a molecular weight of between 100,000 and 800,000, preferably 200,000 to 600,000. The amylopectin fraction of the starch may have a molecular weight of between 400,000 and 5,000,000. Preferably the ratio of amylose to amylopectin is in the range 30:70 to 70:30. Suitable sources of the starch include maize, waxy maize, high amylose maize, potato, wheat and pea starch. In particular applications, particular starches have specific uses. High amylose starches appear to retard drug release in water, acid and $\alpha$-amylase more effectively whilst the opposite is true for high amylopectin or waxy starches. It will therefore be appreciated that the starch-type digestible polymer may be amylose or amylopectin.

The relative proportions of the first polysaccharide and digestible, starch-type polymer is not particularly important but is preferably sufficient to ensure that the composition is resistant to attack by the acidic environment of the stomach. The first polymer is preferably alginic acid or pectin and the digestible, non-gelling polymer is preferably starch. The ratio of alginic acid to starch may be in the range 95:5 to 5:95; preferably 90:10 to 40:60 and especially 85:15 to 50:50. Gel forming compositions having ratios lying outside these ranges may also be used.

It is believed that the compositions containing an entangled active material, which is substantially homogeneously distributed throughout the polymer matrix are new per se. The invention therefore provides an orally administrable, solid, erodible composition comprising an active material and divalent or multivalent cation cross-linked polysaccharide. The polysaccharide gels in the presence of a divalent or multivalent cation to form substantially homogeneously polymeric matrix having cross-linked polymer molecules. Upon formation of the composition the active material becomes entangled in the cross-linked polymer molecules and is uniformly distributed within the polymer matrix. The preferences regarding the quantities and types of polysaccharide employed and the divalent and multivalent cations used to gel the matrix are indicated above.

It is also possible to readily control the crystal or particle size of the active material distributed throughout the matrix compositions. It is believed that the compositions containing crystals or particles of predetermined size distributed in a substantially homogeneous fashion throughout the matrix are new per se. The advantage of controlling particle size means that it is possible to control the rate of dissolution of the active material from the composition. The homogeneity of the dosage forms and the size of the crystals or particles distributed therein can be determined using SEM and TEM. Heterogencity may also be desirable where small particles dissolve before large ones.

Almost any active material can be included in the compositions according to the present invention. Compositions containing both water-soluble and fat-soluble materials may be prepared. In addition to active agents such as drugs, analgesics, non-steroidal anti-inflammatory drugs $H_2$ antagonists, the compositions may also be used to prepare dosage forms containing therapeutic microorganisms or bacterial. Vitamins and minerals, enzymes, genes and gene fragments. The invention can also be used for agrochemicals, enzymes, nucleic acids, seeds, pollen etc. Solids and liquids, such as liquid oils may also be used.

In a first embodiment of the second aspect of the invention the polysaccharide is alginic acid or pectin, combined with gelatinised starch in a variable ratio and the gelling agent is a cation such as calcium. These compositions have remarkable ability to mask the taste of an active material contained therein and control the release of drugs. Because of the unique composition the binding/entrapment/release characteristics of guest molecules can be controlled plus digestibility and site of digestion in the gastro-intestinal tract.

The compositions are able to support a high drug loading without loss of matrix homogeneity. The ratio of active material to polysaccharide may be in the ratio 95:5 to 20:80, preferably 80:20 to 40:60 and especially 75:25 to 50:50. Ratios outside these ranges may be used if appropriate.

Additional ingredients may be added to the composition of the invention. These may include flavourings, digestion facilitators, digestion inhibitors, disintegrants and lubricants. Examples of suitable additional ingredients have been referred to above. It will be appreciated that the use of these additional ingredients makes it possible to modify the type of release or facilitate further processing of the composition.

The release profile of the compositions of the invention may be readily modified by the inclusion of a digestible starch-type polymer. A second embodiment of the second aspect of the present invention therefore further comprises a starch-type, digestible polymer. The polysaccharide and starch-type digestible polymer together forming a gel in the presence of a divalent or multivalent cation to form a cation cross-linked polymer matrix. The active material becomes entangled in the polymer chains and retained thereby. Starch has the capacity to form physical entrapment, double helices and inclusion complexes to trap guest molecules. The active material may be uniformly distributed through out the matrix. The dosage forms are substantially homogeneous in character. Suitable starch-type digestible polymers are indicated above together with the relative proportions of the polymers and polysaccharides used.

Preferably the starch-type digestible polymer has the ability to reinforce the composition by forming an interpenetrating network and optionally increasing the extent of cation cross-links within the polymer matrix. Compositions in which the polymer is a starch, starch derivative or $\alpha$-glucan have been found to be particularly good at this.

A preferred embodiment of the second aspect of the invention therefore provides a composition in which the digestible polymer is starch or a starch derivative thereof or $\alpha$-glucan. The nature of the starches employed and their effects on the dissolution profiles achieved have been discussed above. Depending upon the nature of the starch used, the active material may be present in a form in which it is entrapped by gelatinised or partially gelatinised starch; complexed with amylose chains; or entangled within the alginate and starch strands. Amylose and high amylose starches are particularly effective in reinforcing the alginate matrix. It is assumed that this is because amylose readily retrogrades and complexes from solution.

As indicated above, the starch may be in gelatinised or partially gelatinised from. Starch substantially resists attack by the acidic media found in the stomach, but is susceptible to attack by amylase enzymes and micro-organisms present in the ileum and colon, respectively. It will therefore be appreciated that the addition of starch makes it possible to prepare compositions having a wide range of release characteristics. The nature of the release obtained therefore depends, in part, upon the type of starch used to form the composition. It will therefore be appreciated that release of active material is dependent upon the digestibility characteristics of the composition rather than pH changes that occur through the gastro-intestinal system.

The ratio of active material to total polysaccharide content may be in the range of 95:5 to 20:80, preferably 80:20 to 40:60 and especially 75:25 to 50:50. By total polysaccharide it is to be understood to mean the total amount of gelling polysaccharide and digestible, non-gelling polymer. By gelling the polysaccharide it is to be understood that the polysaccharide gel as a consequence of cross-linking brought about by interaction of the polysaccharide with a divalent or multivalent cation.

The compositions according to the first and second aspects of the invention are easily prepared and a third aspect of the present invention provides a novel method for the preparation of the compositions of the invention comprising the steps of forming a solution of the gelling polysaccharide, intimately mixing a sufficient amount of the gelling polysaccharide solution with an active material to form a paste, dispersing the paste in the polysaccharide solution to form a homogeneous dispersion of the active material in the polysaccharide solution and mixing the homogeneous dispersion with a source of divalent or multivalent cations to from a gel. Upon drying the gel a solid composition is formed.

The gel may be dried in a conventional oven. Alternatively it may be freeze dried or dried in a fluidised bed. The compositions are suitably dried at a temperature at which the active material is not degraded. Drying temperatures of between 300 and 80° C. may be used, preferably between 40° and 60°C.

Using the method according to the third aspect of the invention it is possible to prepare substantially homogeneous compositions having the active material distributed throughout the matrix in a uniform fashion. Compositions having the ability to mask the taste of an active ingredient included therein may be also be prepared using the method according to the third aspect of the invention. The method also makes it possible to prepare compositions in which the crystal size of the active material within the matrix can be readily controlled. Active material comprising particles of different predetermined sizes may also be included in the compositions formed. The ability to control size of the active material in the composition greatly facilitates the ability to control the rate of dissolution of active material therefrom. These compositions are also extremely resistant to attack by the acidic environment of the stomach. They are also able to mask the taste of active materials included therein and are suitable as controlled release compositions. The polysaccharide solutions suitable for the preparation of the compositions of the invention are indicated above.

Solutions of alginic acid or pectin give particularly good results. In a preferred embodiment of the third aspect of the invention the polysaccharide solution comprises a solution of alginic acid. It is preferred to use solutions containing cations such as calcium ions to gel the compositions of the present invention.

It will be appreciated that the gelling properties of the solution will be dependent upon the strength of the alginic acid solution. The gelling behaviour of highly concentrated solution may be difficult to control, whereas if the solution is weak, the gelling times may be long and result in gels of inadequate strength. Suitable solutions of alginic acid have a concentration of between 0.5 and 10%, preferably between 1.0 and 6.0% and especially between 1.5 and 2.5%. Particularly good results have been obtained with solutions containing 2% by weight of alginic acid.

The gelling properties of the solution are also dependent upon the source and concentration of cations. Sources of calcium are preferred. Faster rates of gelation are achieved with more soluble sources of calcium such as calcium chloride; higher concentrations also increase the rate of gelling. Conversely the rate of the gelling is much slower with less soluble calcium sources such as calcium gluconate. Suitable solutions of calcium sources have a concentration of between 0.3 and 5.0% by weight. Particularly good results have been obtained with solutions containing 2% by weight of calcium chloride.

In the preparation of compositions having digestible, starch-type polymer it may be desirable to prepare a solution of the digestible, starch-type polymer and to combine this solution with the gelling polysaccharide solution before or after formation of the paste containing the active material. Alternatively, it may be desirable to prepare a solution containing both the gelling polysaccharide and the digestible, starch-type polymer prior to formation of the paste. The relative proportions of polysaccharide and starch-type polymer solutions will depend upon the overall solids contents and the desired composition of the final dosage form. It is preferred to use solutions having the same concentration of both the polysaccharide and the digestible, starch-type polymers.

Suitable digestible, starch-type polymers have been discussed above. Solutions of these polymers may have a concentration of between 0.5 and 10% by weight, preferably between 1.0 and 6.0% and especially between 1.5 and 2.5%. Particularly good results have been obtained with solutions containing 2% by weight of starch. Solutions of gelatinised or modified starches may be used.

Mixing the homogeneous solution with a source of divalent or multivalent cations may be achieved by extruding the polysaccharide solution into a solution of the cations or by slowly adding the cation solution to the polysaccharide solution.

Alternatively, the polysaccharide solution may be placed in a container having a source of divalent or multivalent cations, which can diffuse into the polysaccharide solution thereby causing it to gel. Reproducible results can be achieved by extruding a solution of polysaccharide into a solution of calcium chloride and in a preferred embodiment of the third aspect of the invention of the compositions are produced by extruding a substantially homogeneous dispersion of active material in an alginic acid solution into a solution of calcium chloride. It is especially preferred to use 2% by weight alginic acid and calcium chloride solutions respectively.

The cation may be injected into the polysaccharide solution with the drug. Using this approach, all of the drug is located within a polysaccharide matrix.

In the preparation of compositions containing a substantially soluble active material loss of active material may occur by diffusion upon mixing the dispersion of active material in polysaccharide solution with a source of a divalent or multivalent cations. To prevent loss of active material, the source of cations is prepared so that it is also saturated with respect to the active material. This prevents diffusion of the active material from the composition upon mixing. Particularly good results have been achieved by extruding a dispersion of active material in a solution of alginic acid into a solution of calcium chloride that is also saturated with respect to the active material. It is especially preferred that the alginic acid and calcium chloride solutions are each 2% by weight respectively.

Loss of active material by dissolution may occur upon formation of the paste and formation of the polysaccharide solution. This may be due to diffusion of the active material to the surface of the matrix where it crystallises. this means that the active material is no longer homogeneously distributed throughout the matrix and the crystal or particle size of the active material remaining within the body of the matrix is diminished by an unknown extent. Such diminution makes it more difficult to control the nature of release; in particular, a sustained release profile becomes more difficult to achieve. This loss can be overcome by using relatively large crystals and/or preparing the polysaccharide solution so that it is saturated with respect to the active material. Upon formation of the paste and the subsequent dispersion thereof in the polysaccharide solution, loss of active material through dissolution is minimised. The size of any particles or crystals of active material included in the matrix form is retained. This ensures that a high drug loading can be maintained. As before, particularly good results have been achieved by preparing solutions of polysaccharide that were saturated with respect to the active material, forming a paste from a small amount of active/polysaccharide solution and crystals or granules of the active material and dispersing this paste in the remainder of the active/polysaccharide solution before extruding into a solution of calcium chloride. It is preferred to use alginic acid as the polysaccharide. Preferably both the alginic acid calcium chloride solutions are 2% by weight respectively. Preferably the calcium chloride solution is also saturated with respect to the active material. It is therefore possible, using the process according to the invention to prepare compositions in which the crystal size of the active material can be readily controlled. The benefits of controlling the crystal size and distribution throughout the matrix form have been discussed above and include a greater control over both the nature and the rate of release of the active material therefrom.

In a particularly preferred embodiment of the third aspect of the invention a 2% solution of alginic acid or a 2% solution of alginic acid and starch is prepared which was saturated with respect to the drug (active material). This solution is used to prepare a paste with the active material by intimately mixing the drug (active material) in powder or crystal form with sufficient drug-saturated polysaccharide solution in a pestle and mortar. The paste formed is then admixed with the remainder of the drug saturated polysaccharide solution gently homogenised to form a homogeneous dispersion. The dispersion is then extruded into a solution of a divalent or multivalent cation that is also saturated with respect to the drug (active material). A 2% solution of calcium chloride is especially preferred. The beads formed on extrusion were collected and dried as described previously. The compositions prepared according to this method contained particles of active material of a uniform size substantially homogeneously distributed throughout.

It has been found that by using the method according to the third aspect of the invention, it is possible to prepare compositions having a high drug loading. In addition, the active material is distributed throughout the matrix in a substantially homogeneous manner.

In the method of the present invention the polysaccharides, drugs and cations can be mixed together, allowed to settle and then dried rather than extruding into a $CaCl_2$ (or other salt) solution. Also, into the volumes of the polysaccharide drug mixture, the cation and drug can be injected whereupon the gelling is initiated from within the gel with no surface material.

A variety of compositions can be prepared using the method according to the third aspect of the invention. These include granules, strands, tablets, capsules, dragees and powders. Granules and powders may be suitably be further included in foodstuffs, which may then be administered to patients.

The invention also provides a composition according to the second aspect of the invention for use in therapy.

In yet a further aspect of the invention there is provided a method of therapy comprising the administration of a therapeutically effective amount of a composition according to the second aspect of the invention to a patient requiring therapy.

The invention further comprises the use of a composition according. to either the first or second aspect of the invention for the preparation of a medicament for use in therapy.

The invention additionally provides a kit for the preparation of compositions according to the first and second aspects of the invention comprising a performed paste of an active material in a polysaccharide solution, a solution of polysaccharide and a source of divalent or multivalent cations. It is especially preferred that the kit further comprises a container which includes the source of divalent or multivalent cations such that when the paste and polysaccharide solution are mixed together in a container, the cations present therein diffuse into the homogeneous dispersion so formed causing it to gel and entangle the active material into the polymer network so formed. The gels so formed may then be administered to a patient requiring therapy.

In the present invention when gels are formed by a mixture of the polysaccharides (gelatinised starch and alginate; gelatinised starch and pectins; gelatinised starch, pectins and alginate) containing other molecules (like drugs, chemical, agrochemicals, nutrient, nucleic acids, lipids, proteins, enzymes, cells, micro-organisms etc.) the characteristics of the constituent polysaccharides can symbiotically interact to make novel delivery systems. The cation gelling polysaccharide can give matrices shape whilst the starch can impart rigidity and enhanced controlled/slow delivery and taste-masking characteristics. In addition, the starch fraction is digestible in the small intestine of man—the other polysaccharide not—and this can further tune release characteristics. In other words, the sum of the polysaccharide mixture characteristics is superior to the individual polysaccharide parts.

Alginic acid is relatively insoluble, whilst the salts are not. The salts (especially sodium) need to be dissolved and mixed with the starch. In the case of pectin, the methylation (esterification) affects cross linking. Hence, low esterification is preferred. The starch must be pre-gelatinised or gelatinised just prior to use. Maltodextrins and other chemically/enzymatically/physically modified starches may be used.

The drug delivery/molecular and microbial release and taste masking characteristics of these matrices can be tuned by varying the source (and hence polysaccharide structure and starch composition) of the starch, alginic acid and pectin fraction.

The starch fraction may be generated from plant breeding, mutations, transgenic technology and may include chemically, biochemically, enzymatically and physically modified starches (including pre-gelatinised, cross-linked etc).

The drug delivery/molecular and microbial release and taste masking characteristics of these matrices can be tuned by varying the ratio of the polysaccharides to one another.

The systems when dry can be loaded with very high levels of guest molecules—more than 75% by dry weight (<25% polysaccharide) which is relatively unique.

The materials can be formed as pellets (dripping droplets into appropriate salt solutions), strands, sheets etc (by extruding directly into the salt solution).

Unlike other polysaccharides, α-glucans are digestible in the small intestine of man and animals by the (pancreatic) amylases. Other polysaccharides and resistant starches can, however, be fermented in the large intestine to release guest molecules in this organ.

Both hydrophillic and hydrophobic molecules (including drugs) can be successfully entrapped with these matrices. In essence, all molecules can be entrapped.

Liquids (like oils) can also be entrapped with these matrices.

The polysaccharides are relatively inexpensive, freely available and food grade.

By extruding the polysaccharides into a salt solution containing dissolved (saturated) active (e.g. drug), the size of the drug crystals in the matrices gelling in the salt solution can be retained.

The release of the active ingredient from the polysaccharide matrix is diffusion dependent, which is a function of the drug/molecule crystal size in the matrix and its own inherent solubility.

It will also be appreciated that the invention finds application in other fields of use such as the release of fertilisers and dyes.

The invention will now be described by reference to the following examples. Variations of these examples falling within the scope of the invention will be apparent to a person skilled in the art.

The invention is also illustrated with reference to the accompanying figures.

BRIEF DESCRIPTION OF THE DRAWINGS

In the figures:

Figure 1:
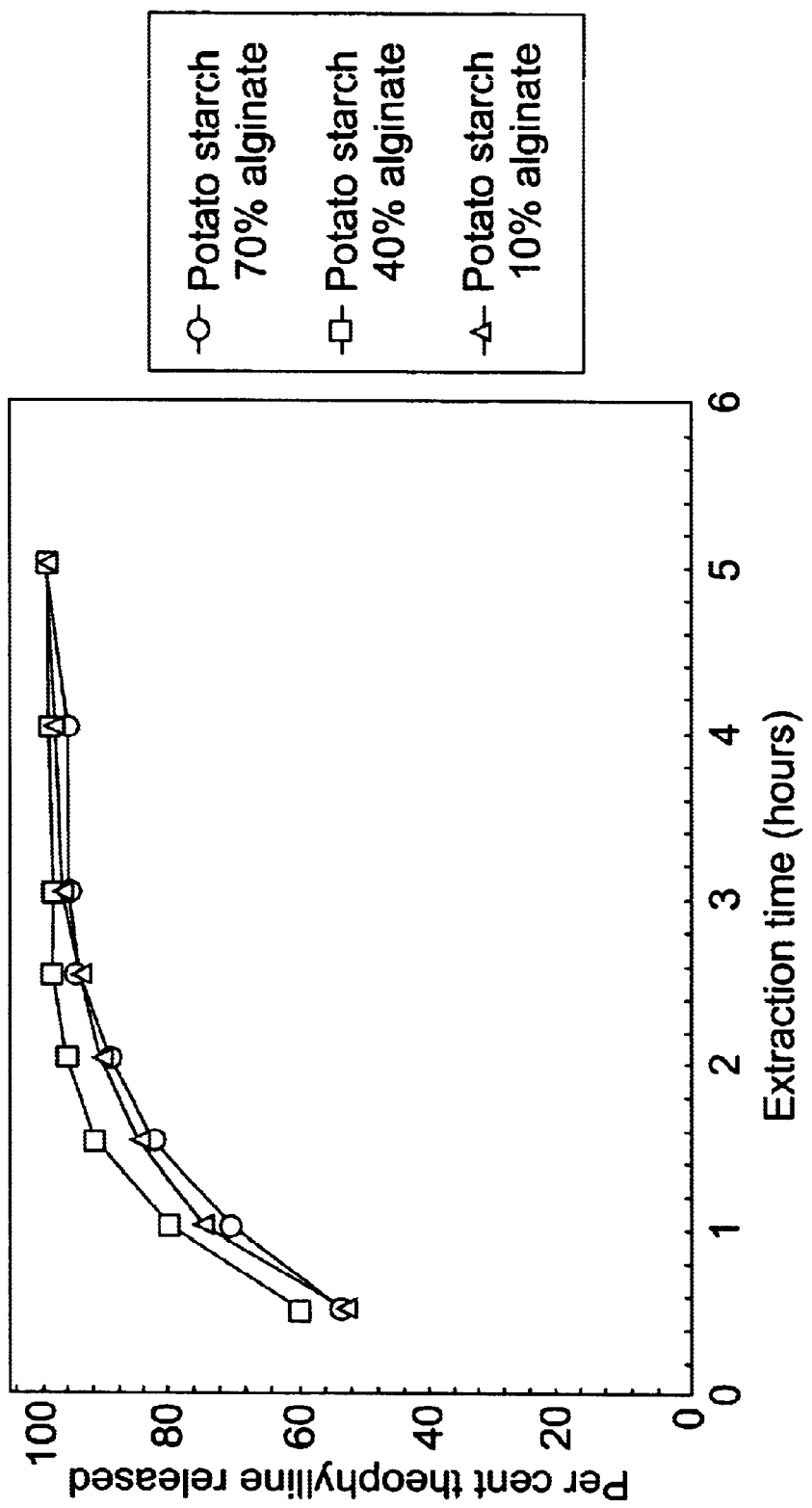
Figure 2:
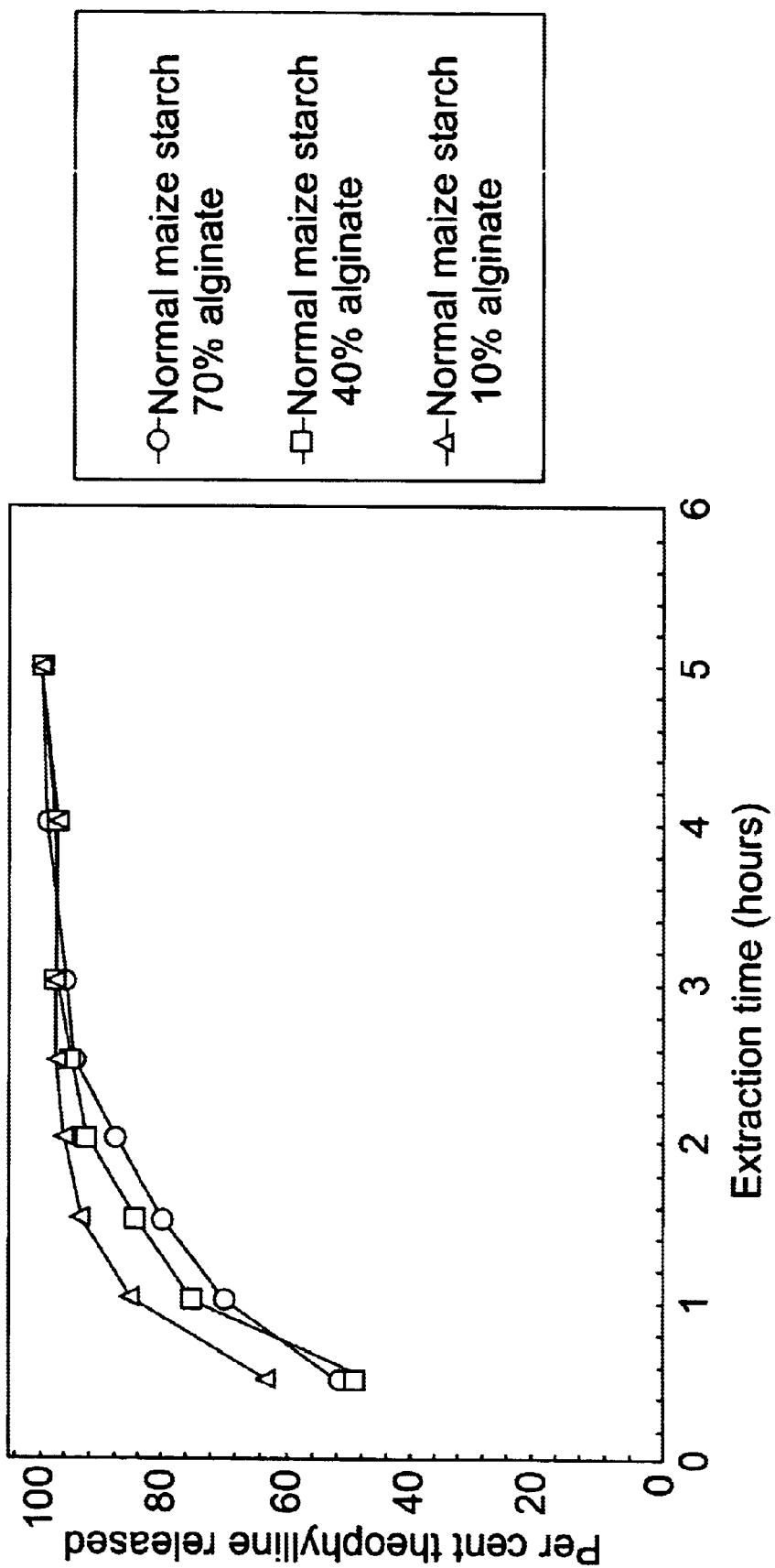
Figure 3:
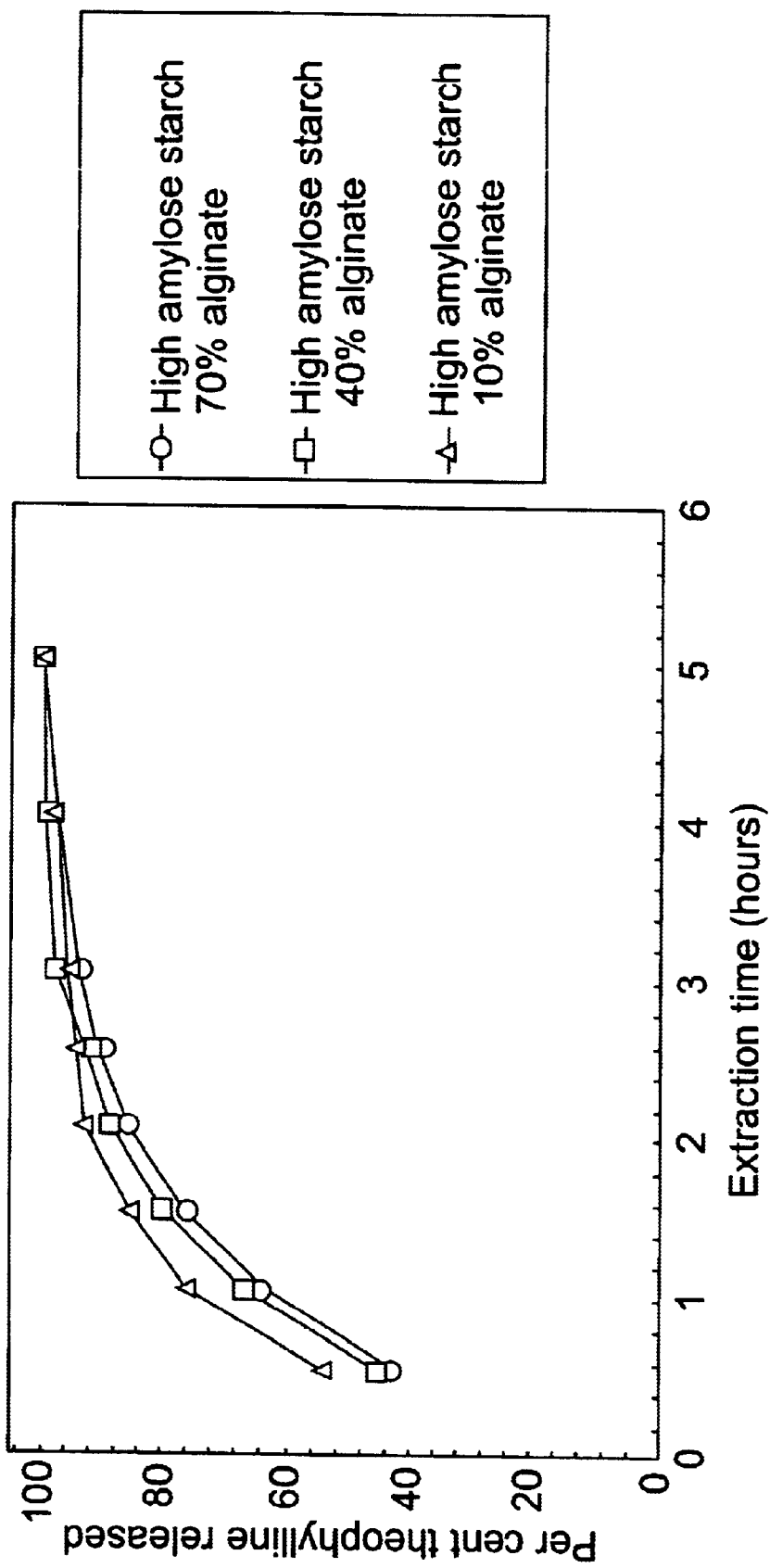
Figure 4:
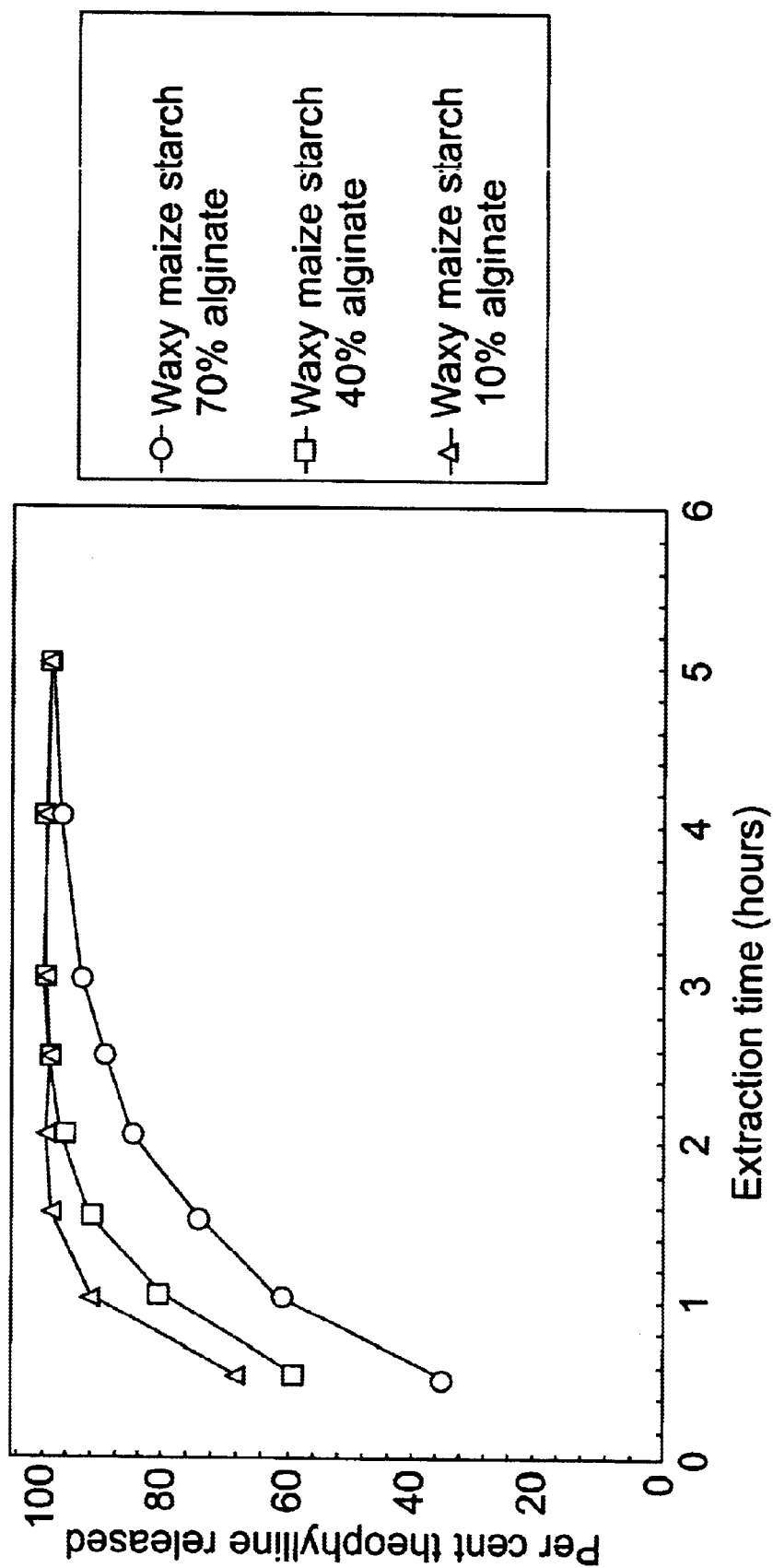
Figure 5:
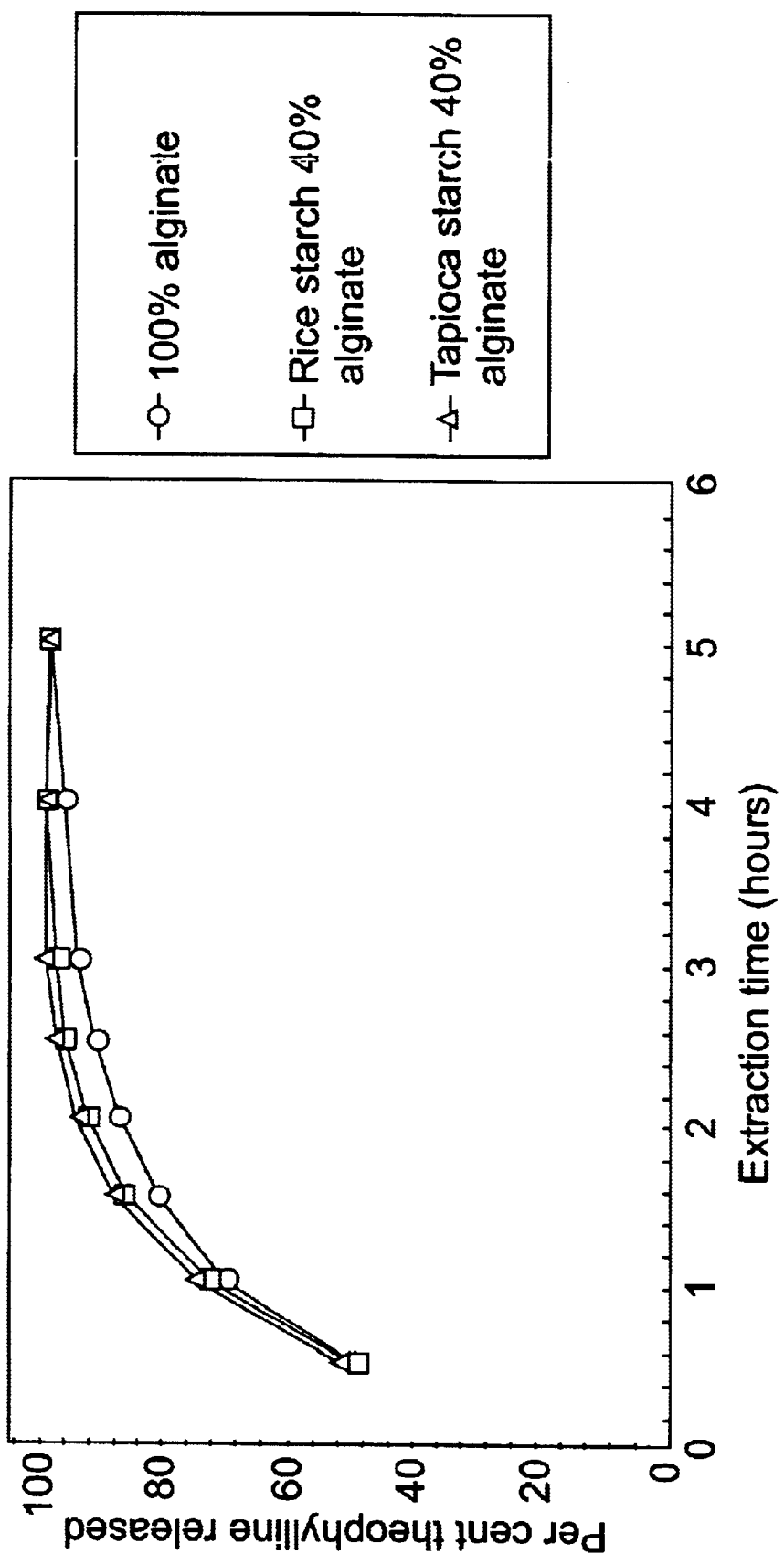
Figure 6:
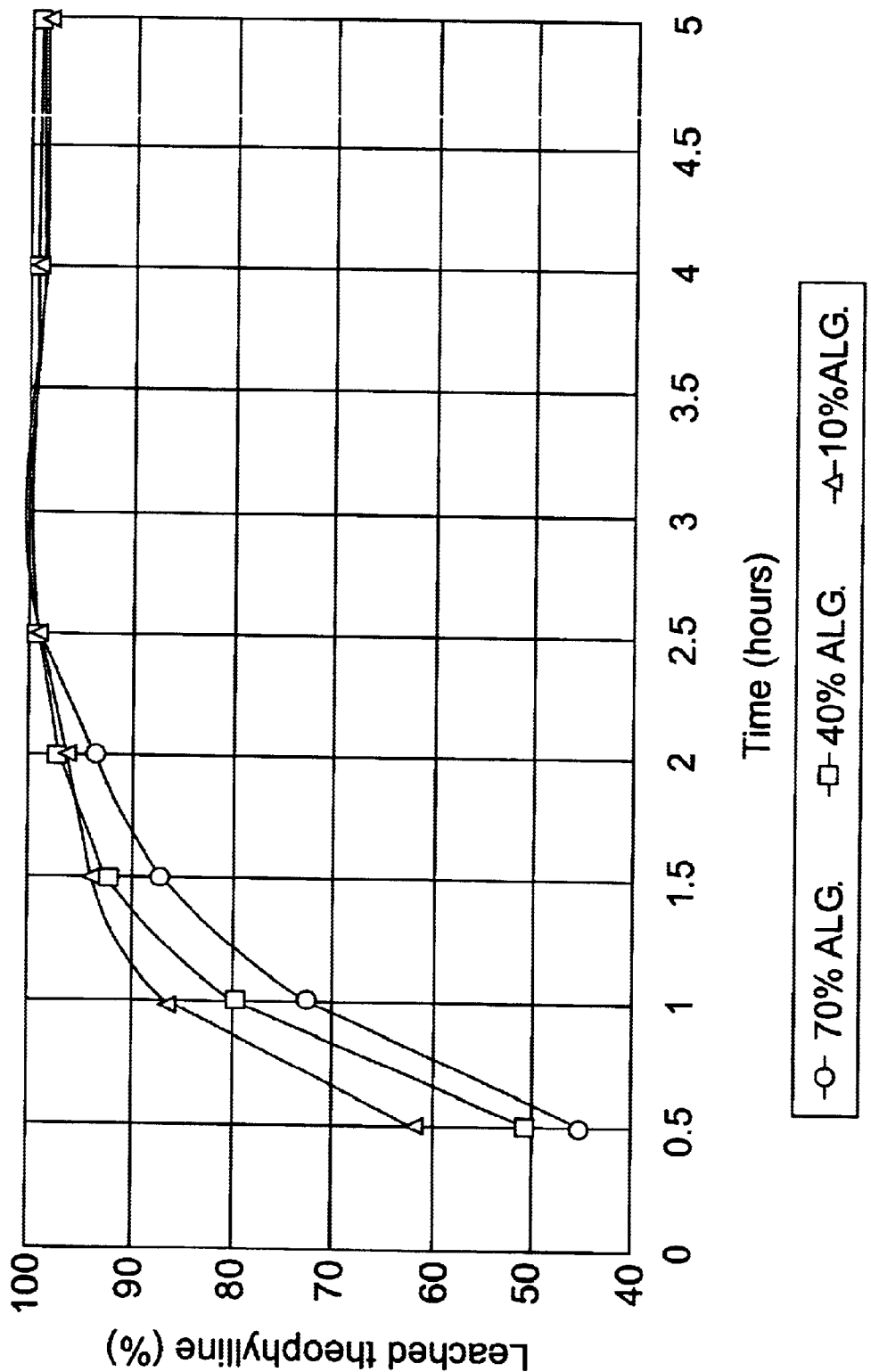
Figure 7:
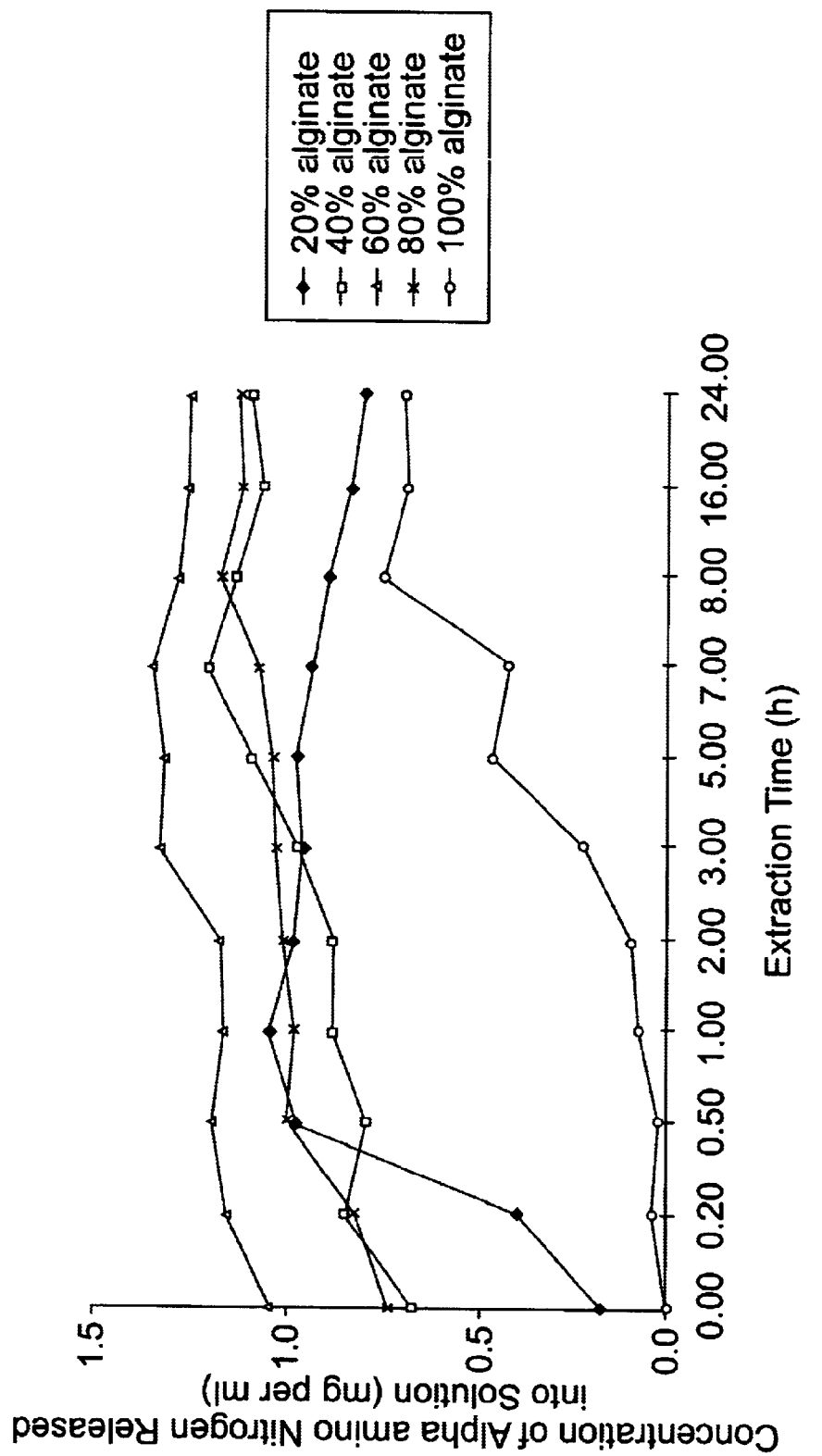
Figure 8:
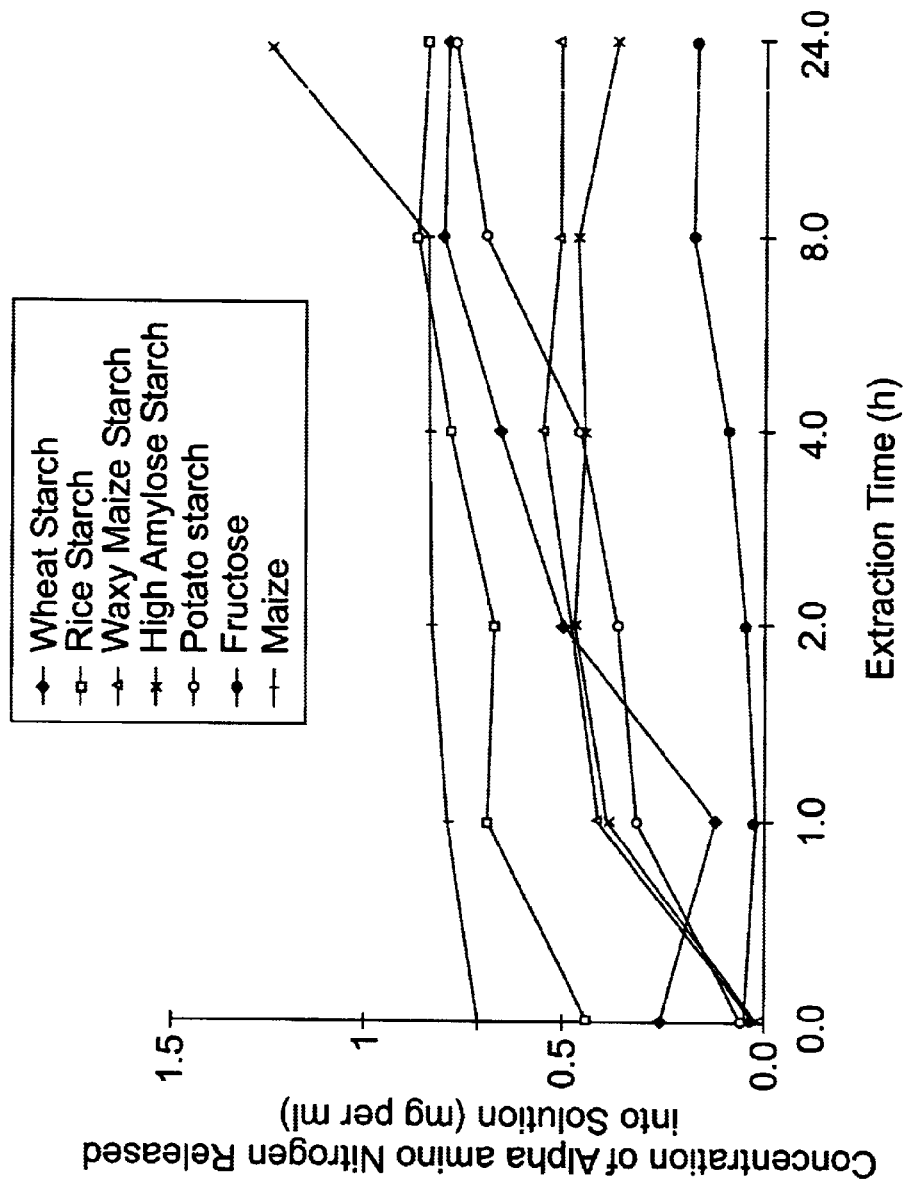
Figure 9:
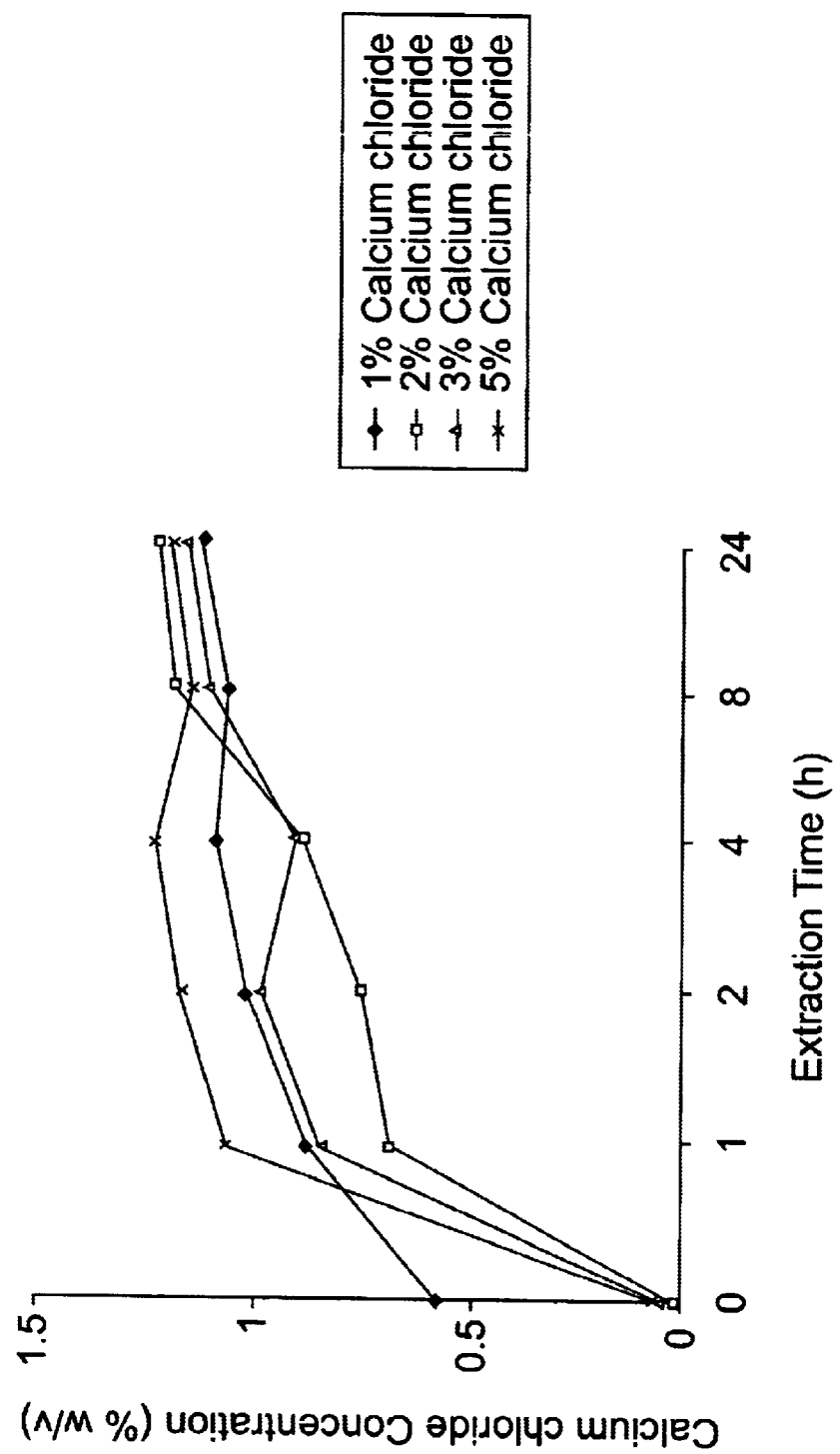
Figure 10:
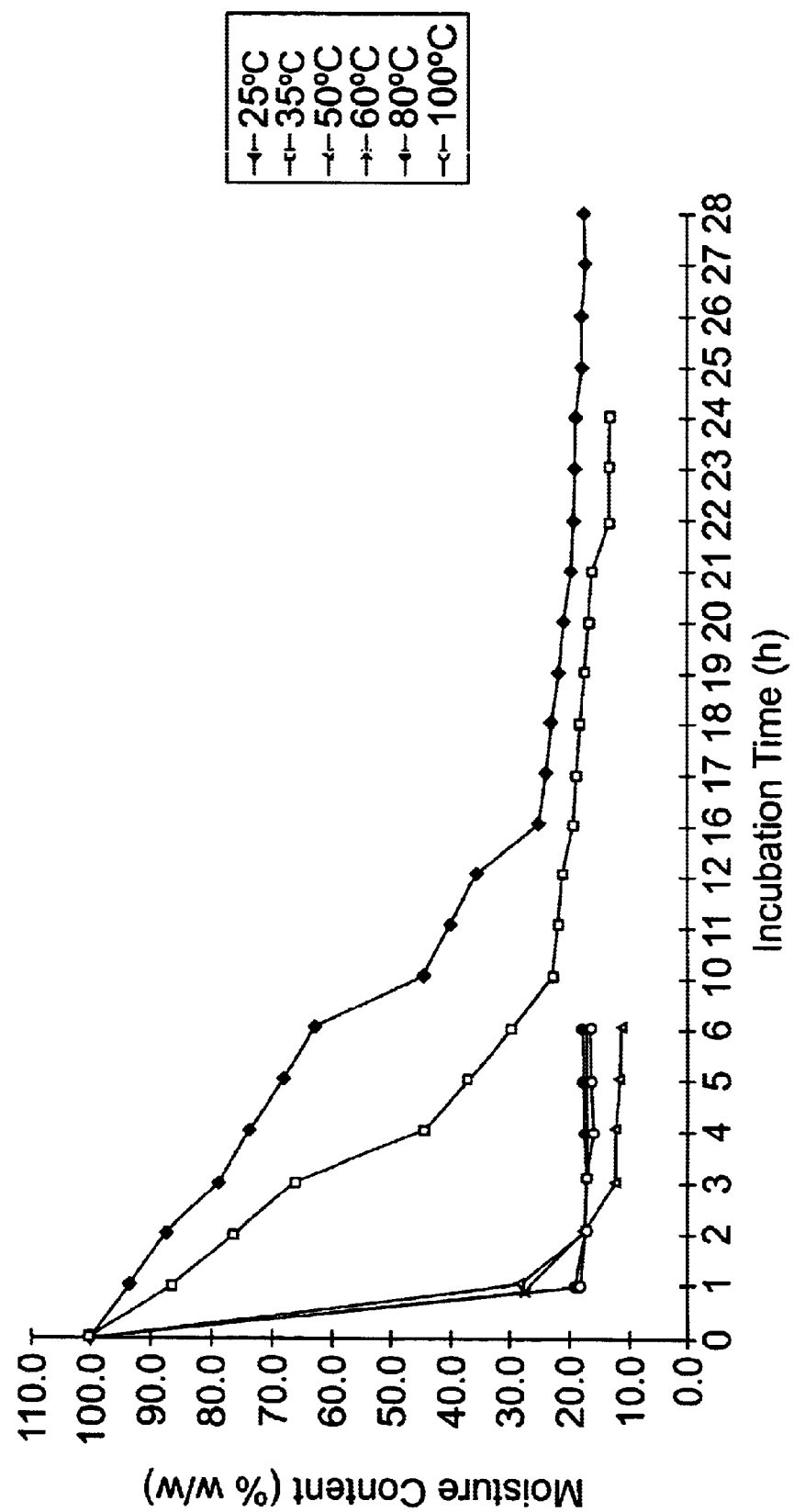
Figure 11:
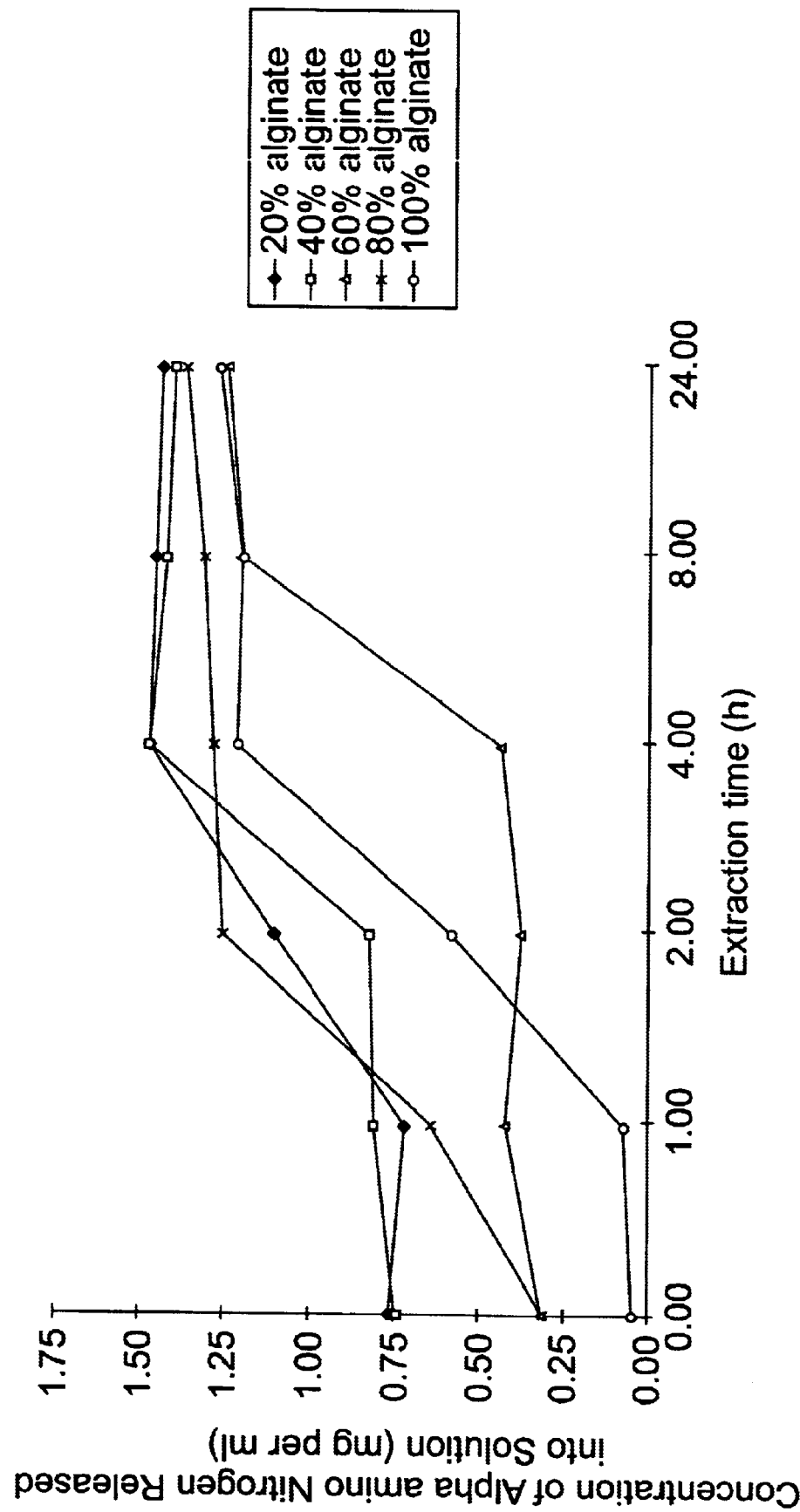
Figure 12:
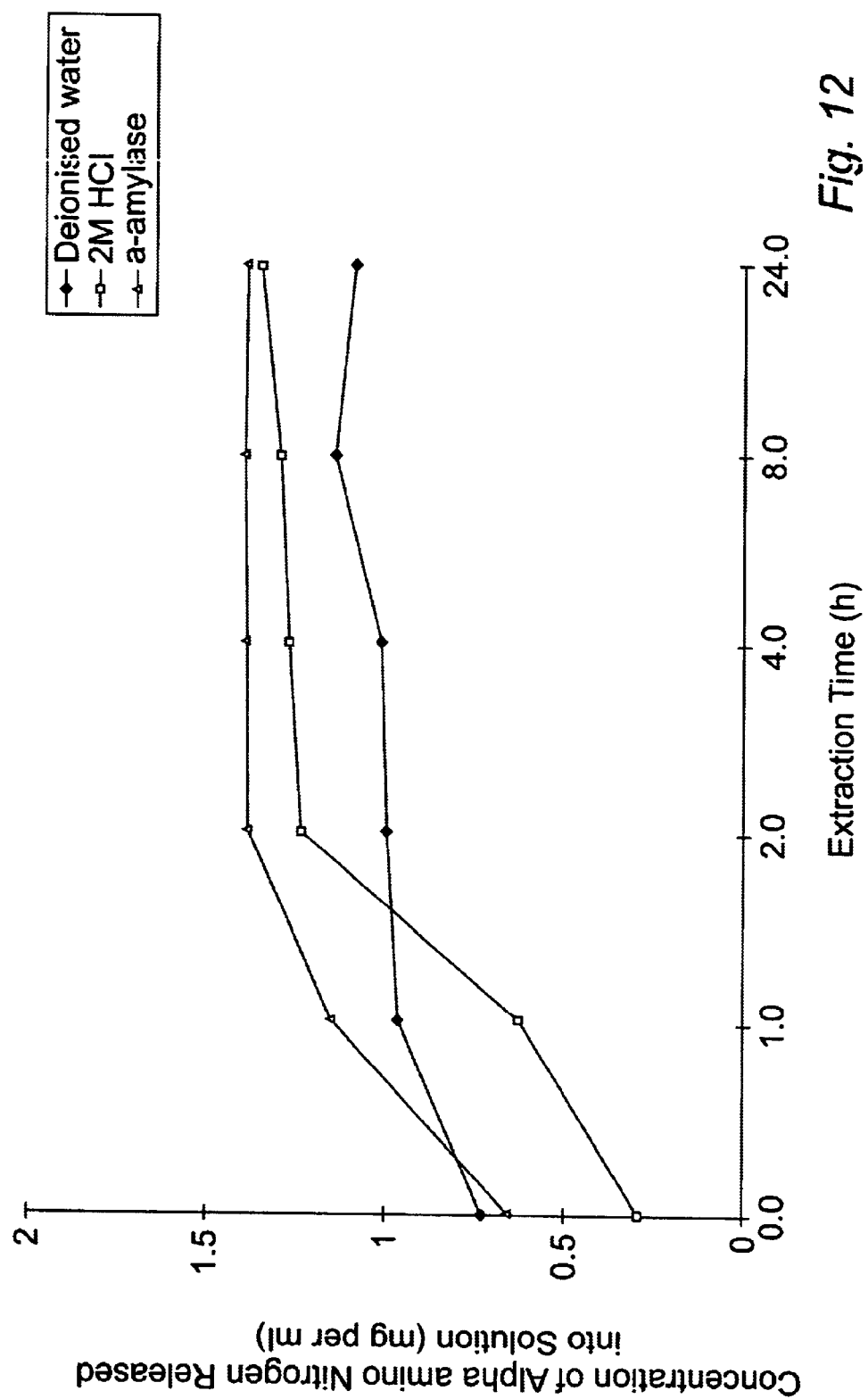
Figure 16:
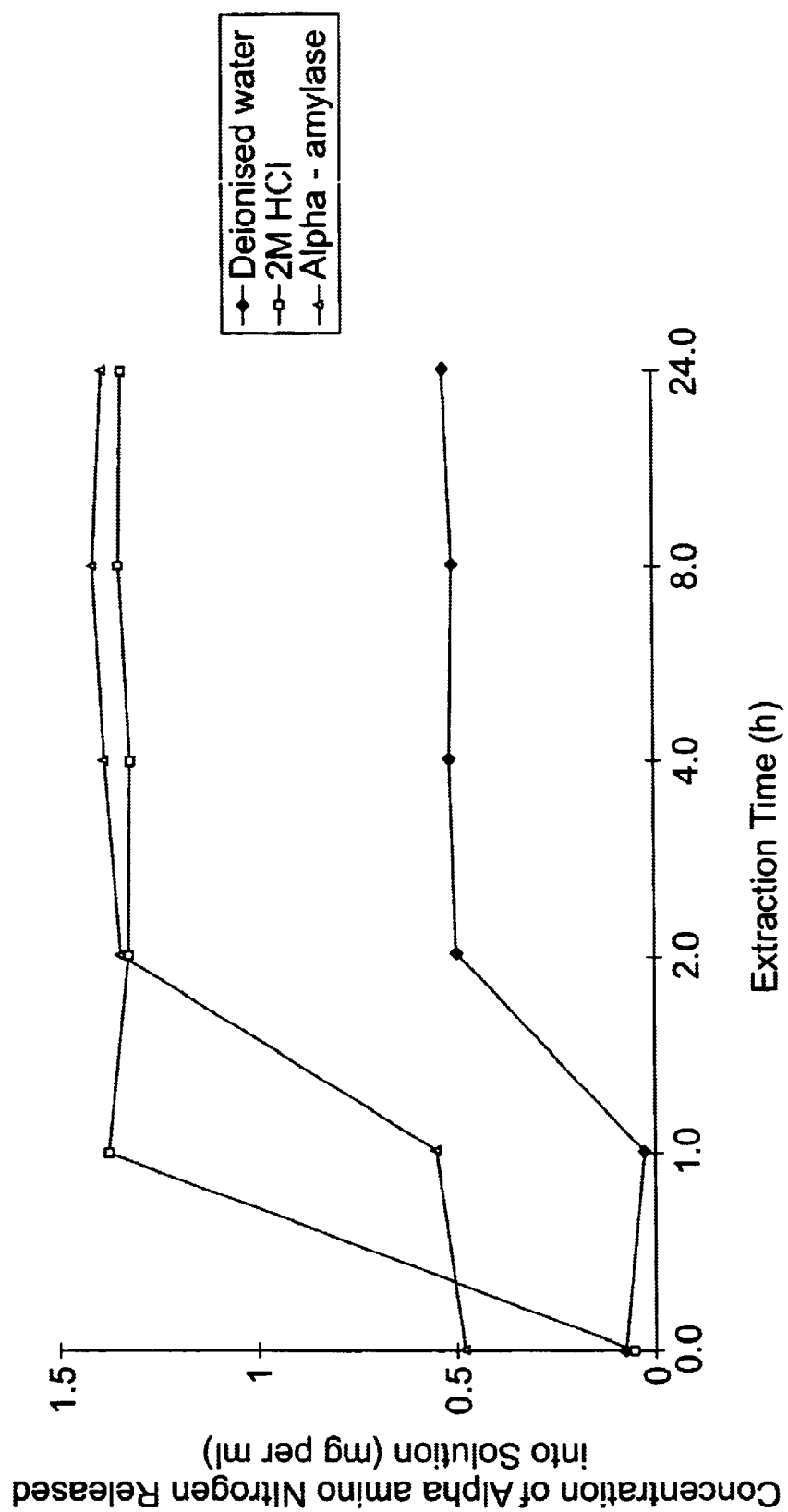
Figure 17:
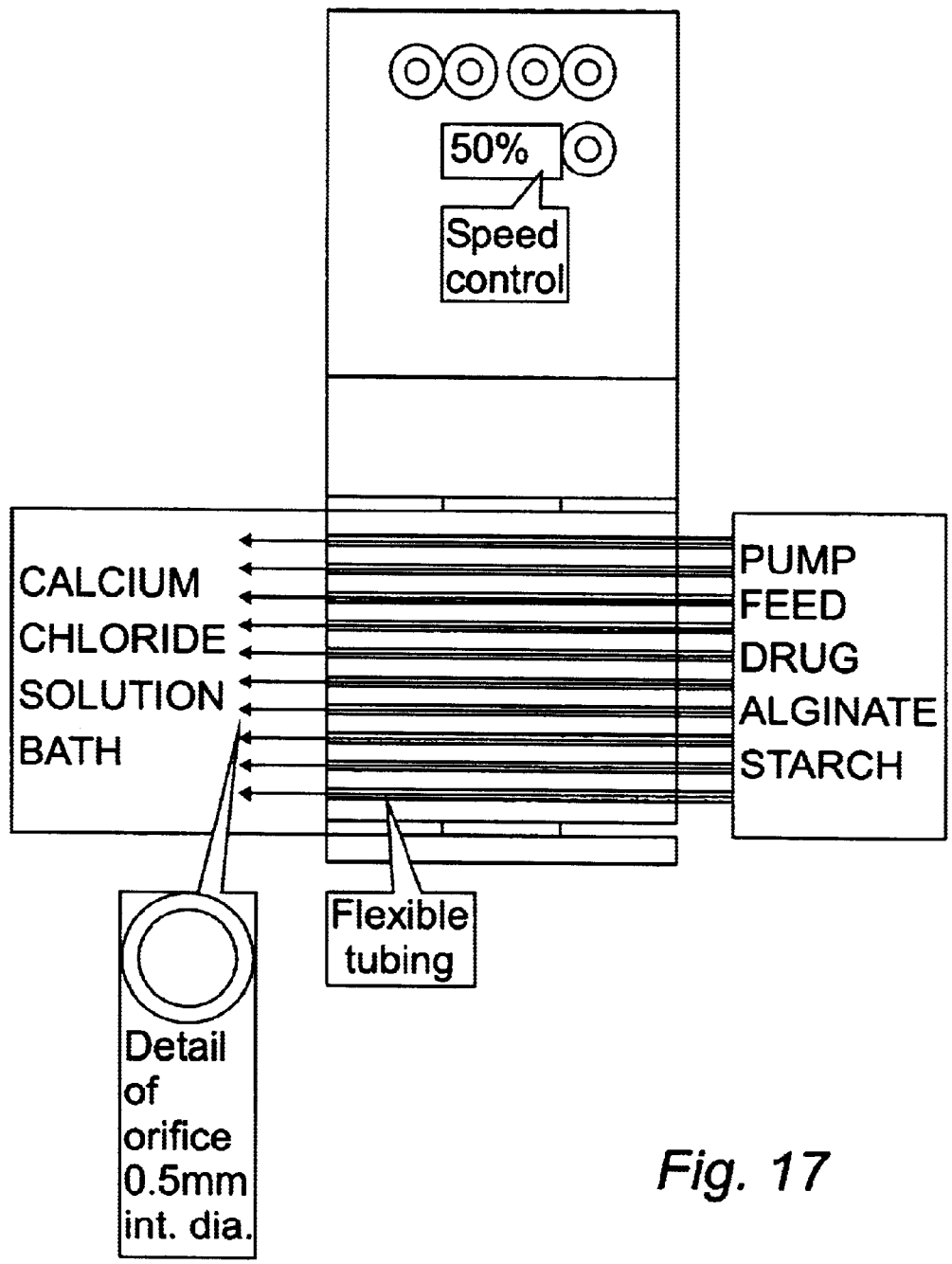
Figure 18:
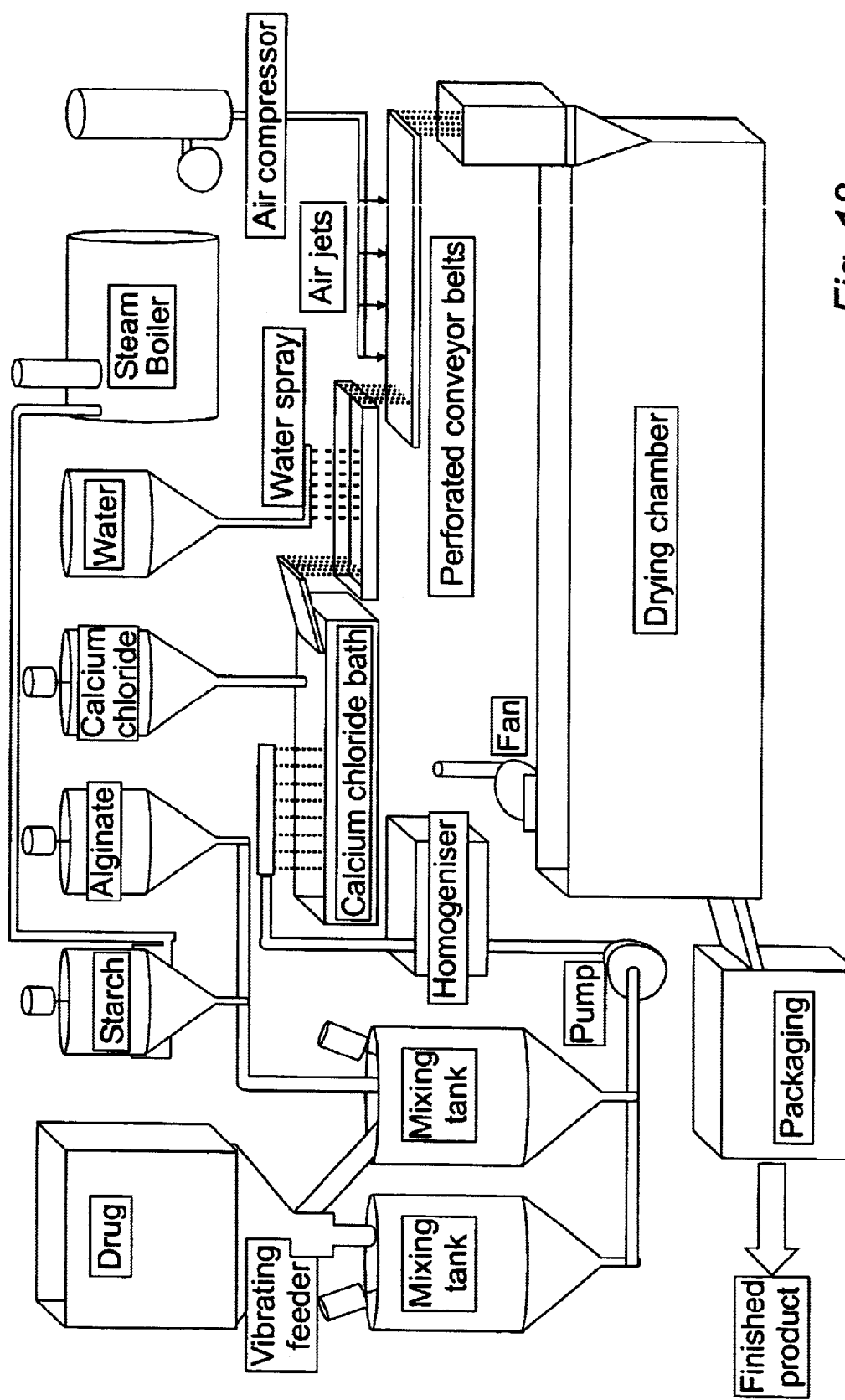

| | |
|---|---|
| FIGS. 1–5 | Illustrates leaching of theophylline from starch-alginate granules in water at 37° C. with shaking. |
| FIG. 6 | Illustrates leached theophylline from maize starch/alginate granules in 40 mL acetate buffer with fungal alpha-amylase. |
| FIGS. 7–9 | Illustrates the release of glycine (as alpha amino Nitrogen) from an Aqueous Suspension of Alginic acid: Starch Beads (1% w/v), prepared using Calcium chloride solution saturated with Glycine. |
| FIG. 10 | Illustrates the effect of drying temperature and the moisture content of moisture content of Alginic acid: Starch Beads. |
| FIG. 11 | Illustrates the release of Glycine on Acid extraction of a suspension of beads. |
| FIG. 12 | Illustrates a comparison of Glycine released from Aqueous, Acid and Alpha-amylase extractions of beads. |
| FIG. 13 | Illustrates release of PKU amino acid mixture from Aqueous suspension of beads. |
| FIG. 14 | Illustrates release of PKU amino acid mixture from an Acid extraction of beads. |
| FIG. 15 | Illustrates release of PKU amino acid mixture from an Alpha-amylase digest of beads. |
| FIG. 16 | Illustrates release of PKU amino acid mixture from beads prepared using calcium chloride solution without saturation of Glycine. |
| FIG. 17 | Illustrates diagrammatically a peristaltic pump for the extrusion of drug alginate starch spheres. |
| FIG. 18 | Illustrates industrial production of starch-alginate-drug granules. |

EXAMPLES

Example 1

Preparations of Compositions (a) Alginic Acid

To 6 g of powdered ibuprofen was added sufficient of a 2% alginic acid solution to form a paste on working the mixture. Alginic acid solution (2%) was then admixed with the paste until 100 ml of 2% alginic acid solution had been added. The resulting mixture was then gently homogenised using a pestle and mortar homogeniser to form a homogeneous dispersion of ibuprofen in 2% alginic acid solution. The homogenised dispersion was then extruded into solution of 2% calcium chloride using a Watson-Marlow 10 channel peristaltic pump extruder to form beads. The beads were separated from calcium chloride solution, placed on a filter paper and dried in a convection oven at 40 C. to form solid, uniform beads.

(b) Alginic Acid and Starch

Compositions comprising alginic acid and starch were prepared according to Example 1(a) above with the modification that a solution containing a total of 2% polysaccharide (alginic acid and starch) was prepared instead of a solution containing alginic acid only. Solutions containing 87.5, 75 and 50% alginic acid on a solids basis were prepared by dissolving in 100 ml of water 1.75, 1.50 and 1.0 g of alginic acid or derivatives thereof with 0.25, 0.5 and 1.0 g of starch respectively.

The above procedures were suitable for the preparation of compositions containing both water-soluble and fat-soluble drugs. Compositions containing aspirin, paracetamol and theophylline have also been prepared using this procedure.

Example 2

(a) Inhibition of Diffusion

Compositions containing alginic acid only or alginic acid and starch were prepared according to Examples 1(a) and 1(b) above. Instead of extruding the dispersion into a solution of 2% calcium chloride, the dispersion was extruded into a solution of 2% calcium chloride that was saturated with respect to the active material.

(b) Inhibition of Solubility

Compositions containing alginic acid only or alginic acid and starch were prepared according to Examples 1(a), 1(b) and 2(a) above. Instead of preparing a solution that contains 2% alginic acid or 2% polysaccharide (alginic acid and starch) a 2% alginic acid or polysaccharide solution was prepared that was also saturated with respect to the active material.

The procedures of Examples 2(a) and 2(b) were particularly useful in the preparation of compositions containing both water-soluble and substantially water-soluble drugs.

Example 3
Properties of Dried Beads
(a) Composition

The beads were dried to <5% moisture. The solid material contained 75% by weight drug and 25% polysaccharide. This ratio was chosen in agreement with other similar delivery system ratios, although it can be varied.

(b) Appearance

The dried beads were white (particularly those containing starch), spherical in shape (ca. 2–3 mm in diameter) with a smooth surface when aspirin and ibuprofen were used as the entrapped drugs. It is probable that complexing as well as physical entrapment within the beads determine the final shape. With theophylline the granules became wrinkled after drying but they retained a uniform size and were free flowing. Granules consisting of 100% alginate were slightly yellow; all other granules containing starch were white.

(c) Resistance of Beads to 0.1M HCl

Bead samples were shaken in 0.1M HCl as above.

(d) Resistance to Fungal α-amylase

Fungal α-amylase was prepared in phosphate buffer 0.1M, pH 6.5) to give a concentration of 100 mg/50 ml (80 units/ml). Bead samples (100 mg) were shaken in 10 ml Sovirel tubes containing 5 ml of enzyme solution with α-glucosidase (added 100 µl of 2.8 mg/ml per tube) at 37° C. for 1 to 24 hours. The tubes were centrifuged (1,500×9) and the amount of solubilised α-glucan was determined in the supernatant as glucose according to Karkalas (1985).

(e) Resistance to Pancreatic α-amylase

This was studied according the protocol described above but the fungal enzyme was replaced with pancreatic enzyme (145 µl1/50 ml, 80 units/ml).

Results (A) Stability in Water at 37° C.

(i) Aspirin and Ibuprofen

When the beads were shaken in water very little leached material could be detected. The beads retained their original form and remained opaque. Beads consisting of 100% alginate were slightly swollen with a transparent surface.

(ii) Theophylline

No major change was noted in the appearance of the granules.

(B) Stability in 0.1M HCl (i) Aspirin and Ibuprofen

The beads were stable to prolonged exposure to 0.1M HCl Very little leached material could be detected. The beads retained their native form.

(ii) Theophylline

Similarly no major changes in the appearance could be observed.

(C) Stability in Fungal and Pancreatic α-amylase (i) Theophylline

Beads containing alginate only were stable to prolonged exposure to fungal and pancreatic α-amylase. Very little leached material could be detected. Beads containing starch were less resistant. Fungal α-amylase has a considerable degrading effect on the starch, but pancreatic α-amylase has a considerable degrading effect on the starch, but pancreatic α-amylase has a less severe effect.

The present application is concerned with compositions for oral administration having the ability to mask the taste of an active ingredient contained therein as well as methods for the preparation of such compositions and their use in the administration of a wide variety of active agents.

Example 4
Taste Masking of Compositions

Compositions comprising 75% of ibuprofen and 25% of polysaccharide were prepared according to Example 1 of GB 9808595.4. Polysaccharide containing 100, 87.5, 75 and 50% alginic acid and 0, 12.5, 25 and 505 starch respectively were used.

The compositions were administered to 17 healthy volunteers who were asked to give their opinion on the taste and mouthfeel of the compositions prepared. Taste comparisons with ibuprofen per se were carried out.

Results

Each of the subjects expressed surprise at the unpleasant burning sensation at the back of the throat and after taste associated with the ibuprofen per se. In contrast, when the subjects tried the compositions of the present invention, they expressed surprise at being unable to taste the ibuprofen in the compositions and considered that these formulations appeared to have no taste whatsoever. In addition 12 of the volunteers commended upon the pleasant mouthfeel associated with the compositions of the present invention, the sensation being smooth and creamy rather than granular and gritty.

Example 5

1. 100% alginate (mechanical mixing)
2. 100% alginate (mixing in mortar)
3. Potato starch 70% alginate
4. Potato starch 40% alginate
5. Potato starch 10% alginate
6. Maize starch 70% alginate
7. Maize starch 40% alginate
8. Maize starch 10% alginate
9. High amylose maize starch 70% alginate
10. High amylose maize starch 40% alginate
11. High amylose maize starch 10% alginate
12. Waxy maize starch 70% alginate
13. Waxy maize starch 40% alginate
14. Waxy maize starch 10% alginate
15. Rice starch 40% alginate
16. Tapioca starch 40% alginate Samples were prepared by mixing 6 g theophylline and 100 g of solution containing 0.5 g theophylline (ie saturated) and 1.8 g of dry polysaccharide as set out above. Assuming no losses during preparation, rapid washing to remove surface calcium and drying at 55–60° C., the anhydrous products should contain 6.5 g theophylline+1.8 g polysaccharide. Total 8.3 g dry solids. Ratio of drug to polysaccharide=6.5/1.8=3.6, or 78.3%. Assuming 10% moisture in the oven dried beads, 8.3/0.9=9.2 g beads. Therefore, (6.5/9.2)=70.6% drug in dried beads.

The samples indicated above have been tested for drug release (a) in the presence of water and (b) in the presence of fungal α-amylase in Na acetate buffer at pH 4.5 and 37° C. The samples treated with amylase were also tested for starch hydrolysis.

Dried drug/alginate/starch granules have an approximately round shape and a wrinkled surface. The granules (70 and 40% initial alginate) swell fairly rapidly in water to give gelatinous translucent beads, which are very elastic. The wet beads are exceptionally robust and very resistant to disintegration even in a blender.

Dried samples containing 10% alginate (90% starch) give rise to white flakes. This is because of the low viscosity of the theophylline-alginate-starch mixture during extrusion, whereby the droplets spread in the form of discs on impact with the surface of the calcium chloride solution. The resulting Ca alginate/starch/theophylline gel particles assume a lenticular form –4–5 mm in diameter. On drying the lenticular particles collapse into white flakes (<1 mm in thickness) that tend to adhere to each other. In contrast extruded mixtures with 70 and 40% alginate give rise to spherical gel-like beads –3–4 mm in diameter, which dry as free flowing granules.

Over 80% of theophylline trapped in the beads is released in water at 37° C. The higher the proportion of starch the more rapid the release of theophylline. The diffusion of theophylline appears to be slower for beads containing high amylose maize starch (FIG. 2) and waxy maize starch (FIG. 4).

Beads consisting of 100% alginate release theophylline more slowly (FIG. 5). Beads containing theophylline crystals mixed with alginate without trituration release the drug relatively slowly because the large crystals must dissolve before diffusion begins. They also contain less theophylline (6 g instead of 6.5 g) and the rate of diffusion would be lower. In contrast, the release of theophylline from beads whereby the drug has been thoroughly triturated with a pestle and mortar with 2% alginate solution saturated with theophylline is more rapid as expected.

When the granules were dispersed in Na acetate buffer pH 4.5 at 37° C., the release of theophylline was more rapid than in water alone. This is presumably due to two causes. Firstly, the hydrolysis of starch by alpha-amylase will cause disruption of the three-dimensional structure containing the drug, and secondly, the Na ions will replace some of the Ca ions in the gel thus resulting in the weakening of the alginate network (the so-called egg-box structure). Starch containing granules released approximately 90% of the theophylline in 1.5 hours (FIG. 6).

The release of theophylline from pure alginate gels (100%) was significantly faster in Na acetate buffer, probably the exchange of alginate Na for Ca ions weakened the gels. However, the beads retained their integrity, at least visually.

Fick's law of diffusion: dw/dt=–DAdc/dx. Where; dw/dt is the mass of solute diffusing per unit time, A is the area through which the molecules move, dc/dx is the difference in concentration per unit distance (concentration gradient) and D is the diffusion coefficient.

Conclusions

The starch-alginic acid co-extrusion drug delivery system has advantages over alginic acid alone.

Resists acid hydrolysis—for very long periods

Controlled digestibility by amylase in the small intestine

Retrogradation (formation of double helices of α-glucan chains) strengthens matrix Potential to form helical inclusion complexes with some chemical moieties Edible—can be marketed as food as well as a drug delivery system Phosphoester groups on starch potentially retain cation Easy to produce Cheaper than alginic acid alone Disguises taste Whereas the present application largely relates to starch plus alginic acid or pectin useful composition may include starch plus other polysaccharide, alginic acid or pectin plus other polysaccharide and polysaccharide derivatives, including oligosaccharide and monosaccharides.

Such compositions may encapsulate chemicals, drugs, amino acids, proteins, enzymes, antibodies, carbohydrates, lipids, vitamins, minerals, flavours, insecticides, herbicides, fertilisers, radioisotopes, cells (animal and plant), microorganisms, viruses etc.

Composition delivery routes include oral, rectal, vaginal, urinary tract, nasal, by injection, dusting, etc.

Example 6

If strands of the molecular delivery systems are prepared, the can be dried and then gently milled. These also milled/ground particles exert the slow/controlled release/taste masking characteristics. To prove this, a gelatinised maize starch:alginate product (50:50) was prepared containing 75% by weight glucose as strands and sheets. The material was ground in a coffee grinder and tasted by twelve individuals. Compared to a simple mixture, the sweet taste was highly masked.

Native and slightly modified starches (granules) can be entrapped within the polysaccharide matrices, as can sugars. The sweet taste of the sugars is masked by the entrapment. The rate of hydrolysis of the native slightly modified starches is controlled by coating with the alginate-starch or pectin-alginate matrices.

Using pectin in place of the alginic acid, unique release characteristics can be generated which are as variable as the alginate-starch matrices. Demethylated pectin (and polygalacturonic acid) has been used in place of the alginic acid. Depending on the source of the starch, the polysaccharide ratio and the polysaccharide to guest ratio, the rate of release can be controlled. The pectin is preferred in some formulations as alginic acid is not necessarily a flavoured nutrient (particularly in health care products) as it potentially contains contaminates associated with the growth of kelp in the sea. For example:

A 2% solution of maize starch was prepared as normal. Similarly, a solution of pectin (Sigma P-9135 from citrus fruits) was prepared—although 2% was found to be a little too concentrated and 1% was preferred. The solutions were mixed to give the desirable ratio of polysaccharides and guest molecules were added—amino acids, ibuprofen or glucose. The samples were mixed and extruded into calcium chloride as previously reported. Finally they were oven dried at 50° C. It was found that in common with alginate products these materials mask taste.

Entrapment of micro-organisms has been achieved using different Lactobacilli Spp. It has been found that after storage (refrigerated or room temperature) the organisms are still viable.

Mixture of molecules (like different amino acids) can be incorporated into the matrices. These other molecules can enhance/retard the release of the guest molecules.

Oven drying makes relatively rigid matrices, whereas freeze-drying makes very permeable relatively east to hydrate matrices.

Generally the alginate:starch or pectin:starch ratio should not exceed 80:20 as the 'gelled' material becomes very fragile at higher non-starch polysaccharide levels. The preferred operating range is 25:75 to 75:25, although all the other ratios have been investigated.

Also high-amylose starches entrap molecules more forcibly than normal starches which themselves entrap molecules more than waxy starches.

Using microscopy—especially SEM—the distribution on the surface and throughout the matrices of drugs can be seen to be homogeneous.

The release of drugs from the matrices can be further controlled by using a distribution of crystal sizes in the matrices. The smaller crystals diffuse into solution first, whilst the larger crystal take longer to dissolve and diffuse.

Addition of gelling ions to the polysaccharides.

The mixture of alginate:starch or pectin:starch was prepared as normal. This material was pipetted (about 15 ml aliquots) into 20 ml wells (ice cube trays). A solution was prepared containing sugars, minerals or amino acids in a calcium chloride solution. A small aliquot (approximately 100 μl). This material was injected into the 15 ml aliquots and immediately withdrawn. The effect is that gelling proceeds from inside the gel outwards. The gels were then dried. It was found that teflon or similar coatings are necessary to avoid the polysaccharides sticking to the walls of the containers. This approach (the 'pastille approach') has the advantage in that the guest molecules are entrapped within the polysaccharide matrix without any surface crystals. In addition, it was found that lipids interspersed with gelling ions could be injected into the polysaccharides and when the cations caused gellation, the lipids were trapped. This delivery system can carry very high levels of guest molecules—in excess of 75% on a dry basis.

Sodium alginate is a relatively cheap and effective gelling agent. It is symbiotic with starch and forms a coherent matrix.

Polygalacturonic acid (demethylated pectin) is equally freely available, but tends to be more expensive than alginic acid. However, alginic acids have some questionable nutritional attributes because they may have picked up heavy metals from seawater during biosynthesis.

Example 7
RELEASE OF AMINO ACIDS FROM STARCH:ALGINATE BEADS
Summary

1 Alginic acid: maize starch beads were prepared using a range of formulations/procedural modifications with a view to establishing the factors which influence the release of amino acids from them on extraction with deionised water, hydrochloride or α-amylase at 37° C.

2 In deionised water, release of amino acid from the beads is influenced by their alginic acid:starch ratio. Beads made with 40 to 80% alginic acid gave higher yields of extracted glycine than was the case for beads made using 20% or 100% alginic acid. It took longer to achieve maximum extraction of amino acid with the 100% aglinic acid sample than was the case for samples of beads containing less of this polysaccharide. Glycine yields from acid-extracted beads were unaffected by their alginic acid:starch composition.

3 The release of amino acids from beads extracted with deionised water was influenced by the botanical source of the starch used in making them. The lowest yields of extracted glycine were obtained when fructose was used. Beads made using maize starch gave the highest yields of extracted glycine.

4 Niether the calcium chloride concentration used in the gelling bath, or the time the beads were held in the gelling bath prior to harvesting and drying, affected the amount of amino acid released from them.

5 The rate of moisture loss from the beads increased with drying temperature up to 50° C., above which temperature no differences in the rate of moisture loss were observed.

6 A high starch:alginic acid ration is not detrimental to the release characteristics of amino acids from the beads and is, in fact, the preferred composition for the beads as alginic acid is on the "negative list" of acceptable nutrients.

7 Starch:alginic acid beads have the potential to be very useful delivery systems because of their physical properties and potential for the starch—unlike the alginic acid—to be completely digested in the gastrointestinal tract.

Objectives

1 Define the most nutritionally favourable polysaccharide (alginate to starch ratio) to entrap the amino acids using glycine as a reference material.

2 Define the most appropriate gelling bath (saturated salt solution) for this process—using glycine as a reference material.

3 Define the most appropriate drying conditions to stabilise the matrices using glycine as a reference material.

4 Characterise the in vitro leaching characteristics of the beads in water, 2M hydrochloride acid and α-amylase as a function of time using glycine as a reference material.

5 Repeat 1 to 4 using a standardised amino acid mixture provided.

Methods

Alpha—Amino Nitrogen Determination

Solutions

The following solutions were prepared:

a) Ninhydrin Reagent

Into 70 ml deionised water was added, in turn, ninhydrin (0.5 g), fructose (0.3 g), anhydrous disodium hydrogen orthophosphate (10 g) and potassium dihydrogen orthophosphate (6 g). The solution was made up to 100 ml with distilled water and stored at $4°$ C. for up to 1 week in a brown bottle.

b) Ethanolic Potassium Iodate

Potassium iodate (1 g) was added to a water:ethanol mixture (ratio 6:4, v/v) and the mixture stirred for 2 h at room temperature. The suspension was then filtered to remove undissolved potassium iodate and the saturated solution stored in a stoppered flask.

c) Glycine Standard

Glycine (55 mg) was dissolved in deionised water and diluted to give a stock solution of 100 $\mu$g α-amino nitrogen.ml$^{-1}$. A volume (3 ml) was added to a 100 ml volumetric flask. Once diluted, this gave a standard with an α-amino nitrogen concentration of 3 $\mu$g.ml$^{-1}$ for use in subsequent analyses to allow comparison with the standard curve for the assay (not reported).

Procedure

Sample dilutions (1000-fold) or standard solution (in both cases 2 ml) were dispensed into stoppered tubes. Ninhydrin solution (1 ml) was added and the stoppered tubes were covered to exclude light before being placed in a boiling water bath was 15 min. They were then cooled under running cold tap water for 5 min. Ethanolic potassium iodate solution (5 ml) was then added to each tube and tubes were inverted. The absorbance of each tube at 570 nm was then read on a spectrophotometer within 20 minutes. Measurements were performed in triplicate, with appropriate blanks and standard solutions being used.

Preparation of Alginic Acid:Starch Beads:Standard Procedure

Solutions

The following solutions were prepared:

a) 2% (w/v) Starch Solution

Maize starch (20 g) was added to 1 liter of deionised water the resulting suspension mixed in a hot water bath until the starch gelatinised.

b) 2% (w/v) Alginic Acid

Alginic acid, sodium salt (20 g) was dissolved in 1 liter of deionised water using an overhead stirrer fitted with a stainless steel paddle.

c) 2% Calcium Chloride

Calcium chloride (20 g) was dissolved in deionised water (700 ml). Glycine (250 g) was then added and, once this had dissolved, the volume of the solution was made up to 1 liter with deionised water.

Making the Beads

Basic Procedure

2% Alginic acid solution (80 g) was mixed with 2% starch solution (20 g). Glycine (6 g) was then dissolved in this 80% alginic acid/20% starch mixture. The solution was then pumped dropwise into a gelling bath containing 2% calcium chloride/25% glycline solution using a peristaltic pump. The solution in the gelling bath was stirred constantly to prevent resulting beads from coalescing.

After 20 minutes, the gelling bath contents were sieved to collect the beads, which were then spread out on greaseproof paper before being held overnight in a drying oven at 60° C. Once dried, they were harvested. This procedure was also used to prepare control samples which contained the starch and alginic solutions, but lacked the addition of 6 g of glycine.

The above method was modified to produce beads with different compositions, thus a) Beads were prepared as above, but with the following maize starch:alginic ratios (w/w basis): 100% alginic acid, 20% starch/80% alginic acid, 40% starch/60% alginic acid, 60% starch/40% alginic acid, 80% starch/20% alginic acid b) Beads (80% alginate/20% starch) were prepared using starch from wheat, rice, waxy maize, Hylon VII (high amylose maize), potato and "normal" maize c) Beads (80% alginate/20% starch) were prepared using maize starch, but using a range of calcium chloride concentrations in the gelling bath ie 0.5%, 1.0%, 2%, 3%, 5% (all w/v).

d) Beads (80% alginate/20% starch) were prepared which incorporated 6% (w/w) PKU amino acid mixture rather than glycine. In preparing these beads, glycine was not added to the gelling bath solution. Samples of beads were made, each having had different residency times in the gelling bath, namely 1 second, 5 seconds, 30 seconds, 1 minute, 10 minutes and 20 minutes.

For all beads produced for use in this study, control samples were made in parallel which did not incorporate either glycine or PKU amino acid mixture at 6% (w/w).

Extraction Procedures

Three extraction methods were employed in this study. These were;

i) Aqueous Extraction

Beads (100 mg) were weighed into 10 ml screw-capped Pyrex tube. Deionised water (10 m) was then added and the capped tubes were placed in a shaking water bath at 37° C. In the first experiment, tubes were removed from the bath 0 h, 10 min, 30 min, 1 h, 2 h, 3 h, 5 h, 7 h, 8 h, 16 h and 24 h into the extraction. These timings were later amended to 0 h, 1 h, 2 h, 4 h, 8 h and 24 h. On removal the tubes were centrifuged (1000×g, 5 min) before the supernatant was filtered through Whatman No 1 filter paper. It was then diluted (1000 fold) prior to α-amino nitrogen determination.

ii) Acid

Beads (100 mg) were weighed into Pyrex tubes as before and 2M hydrochloric acid (5 ml) was added to each. The procedure for the aqueous extraction was then followed, with tubes being withdrawn from the waterbath 0 h, 1 h, 2 h, 4 h, 8 h and 24 h after the start of extraction. Once removed, the tube contents were neutralised with 2M sodium hydroxide and then filtered and diluted as before.

iii) Enzymic

α-Amaylase (5 ml, 20 units per ml, in sodium acetate buffer, pH 4.7) was added to Pyrex tubes containing 100 mg of sample. The tubes were then placed in a shaking waterbath at 37° C. and tubes were withdrawn after 0 h, 1 h, 2 h, 4 h, 8 h and 24 h. On removal from the bath, the tubes were boiled for 3 minutes to denature the enzyme, and then filtered and diluted as for the aqueous extraction procedure.

Experiments were performed in triplicate with blanks containing water, acid and α-amylase solution only included as appropriate. Glycine standards were run concurrently. For each sample incorporating glycine or PKU mixture in the beads a control group from which the amino acid had been omitted was also studied.

Moisture Loss Determinations

Beads (1.0 g, 4 replicates) containing 80% alginic acid/20% maize starch (w/w) were placed in preweighed aluminium pans and the pans containing the beads were then weighed before being put in an oven at 35° C. The pans were removed from the oven at hourly intervals and placed in a desiccator to cool. They were then weighed before being replaced in the oven until the next sampling time. This process was continued until the samples ceased to lose moisture. Moisture loss experiments were then repeated on the same samples using ovens set at 25° C., 50° C., 60° C., 80° C. and 100° C.

Results and Discussion

Varying the Alginic acid:Starch Ratio

The effect of alginate:starch ratio on the release of glycine (measured as α-amino Nitrogen after aqueous extraction of the beads is shown in FIG. 7. The highest yields of extracted glycine (measured as α-amino N) after 24 h were obtained for beads containing 40 to 80% alginic acid (1.08 to 1.24 mg α-amino N ml$^{-1}$.) Beads containing 20% and 100% alginate had lower final yields (0.78 and 0.68 mg α-amino N ml$^{-1}$, respectively). Most samples had similar initial patterns of release of glycine, achieving maximum levels of released glycine after 5 h of extraction. The beads made from 100% alginic acid, however took longer (8 h) to reach maximum levels.

Varying the Botanical Source of the Starch

The botanical source of the starch used in making beads (80% alginic acid:20% starch) influenced the amount aqueous extract of amino acid obtained from them at 37° C. (FIG. 8). Beads made using fructose gave the lowest yield of glycine (as α-amino N), whilst beads made using maize starch gave the highest. The starches were ranked in order of ascending leached glycine yield as follows; fructose (0.17 mg α-amino N ml$^{-1}$)<high amylose maize<waxy maize<potato<wheat<rice<maize (1.24. mg α-amino N ml$^{-1}$).

Alteration of the calcium chloride content of the gelling bath (FIG. 9) had no effect on the release of glycine (measured as α-amino N) from beads in deionised water, with all four samples achieving-similar final yields of released glycine (1.11 to 1.19 mg α-amino n ml$^{-1}$ after the same extraction period (4 h).

Investigation of the effect of drying temperature on the moisture content of 80% alginic acid/20% maize starch beads (FIG. 10) revealed that the rate of moisture loss increased with increased drying temperature. Thus, the slowest loss in moisture was observed in samples dried at 25° C., where the beads took over 20 h to stabilise. Samples held at 35° C. overnight dried faster, stabilising after 10 h. Samples dried at temperatures of 50° C. and above dried even faster and achieved final values after 3 h. The lowest final moisture content was for samples dried in the 50° C. oven (11.7%, w/w basis), whilst samples dried at 35° C. had a final moisture content of 14.2%. The final moisture contents of samples dried at other temperatures were very similar (16.7 to 18.7%, w/w basis).

Acid extraction of the five samples containing different alginic acid:starch ratios (FIGS. 11) produced final yields of released glycine (1.00 to 1.37 mg α-amino N.ml$^{-1}$) which were similar to those obtained for the same samples under aqueous conditions (FIG. 7). The time taken to achieve maximum release of glycine from the beads was 4 h for all five Alginic acid:starch bead formulations.

Based on the results of the aqueous and acid extractions of the various alginic acid:starch combinations, a sample of beads was selected (80% alginic acid:20% starch ) for α-amylase extraction. The results from this extraction are displayed in FIG. 12, along with the corresponding data for aqueous and acid extraction of the same sample. These results indicate that acid and enzymic extraction of the sample produced a similar final yield of amino acid extract (1.36 and 1.40 mg α-amino N.ml$^{-1}$, respectively), whilst the yield of extracted glycine from the aqueous procedure was lower (1.11 mg α-amino N.ml$^{-1}$). The maximum yield of extract for the sample was 4 h regardless of extraction method.

Figure 13:
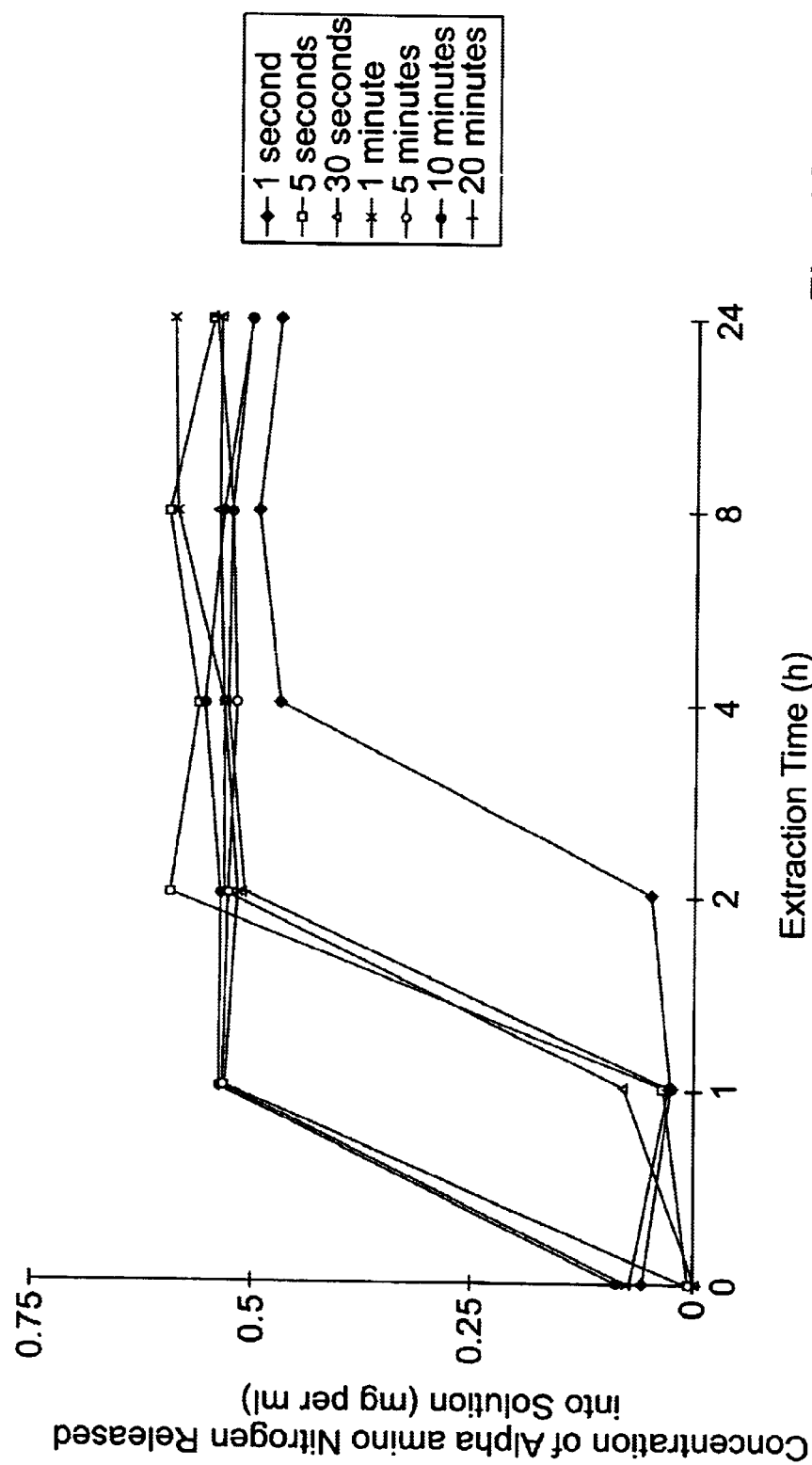
Figure 14:
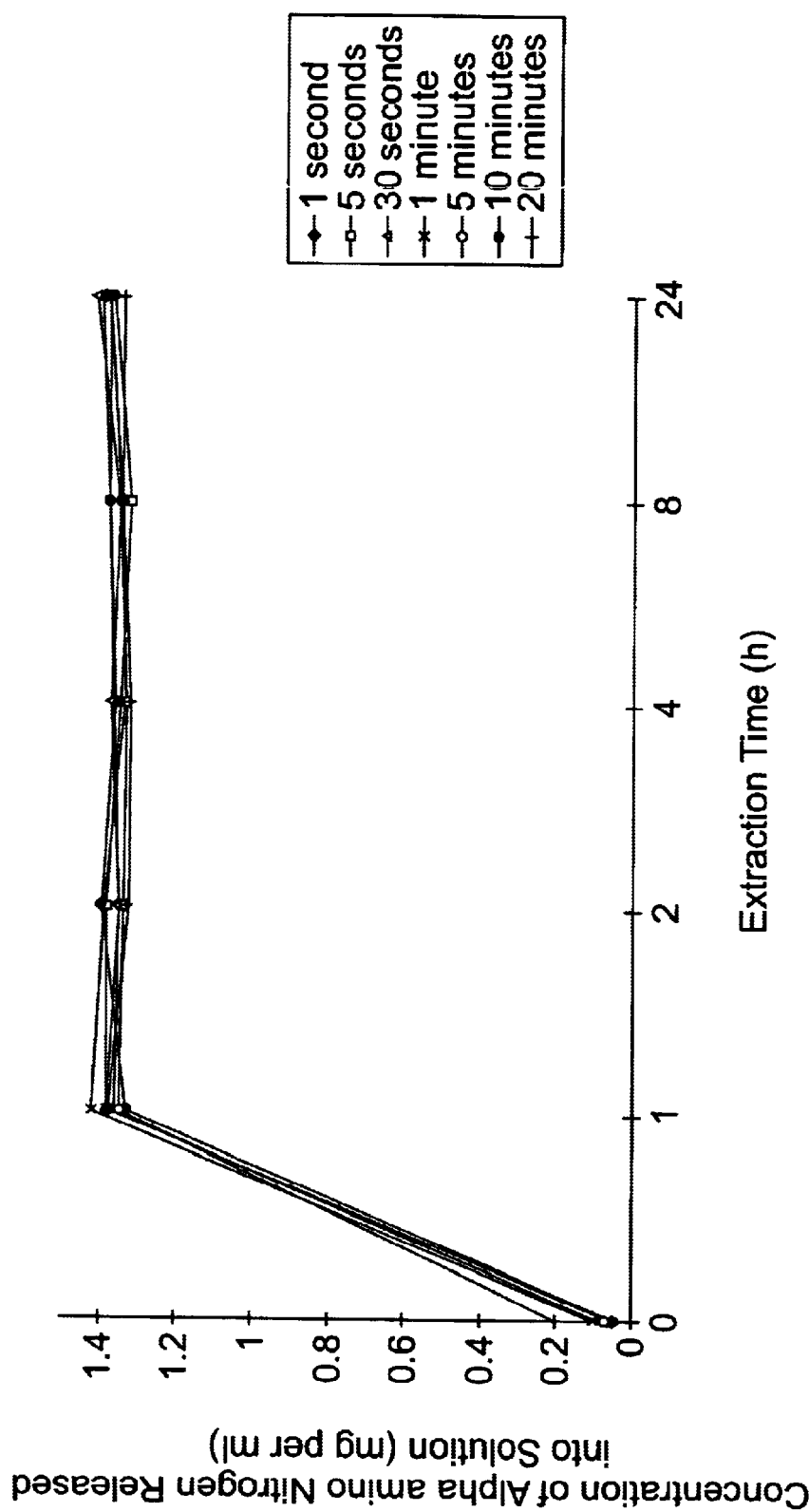

The time that beads spent in the gelling bath had no effect on the pattern of release of PKU α-amino acid mixture (measured as α-amino N) into deionised water (FIG. 13). The final yield of extracted PKU mixture (as α-amino N) was similar (0.47–0.59 mg α-amino N.ml$^{-1}$) regardless of the residency time, as was the time taken to attain that final concentration (1 h).

Figure 15:
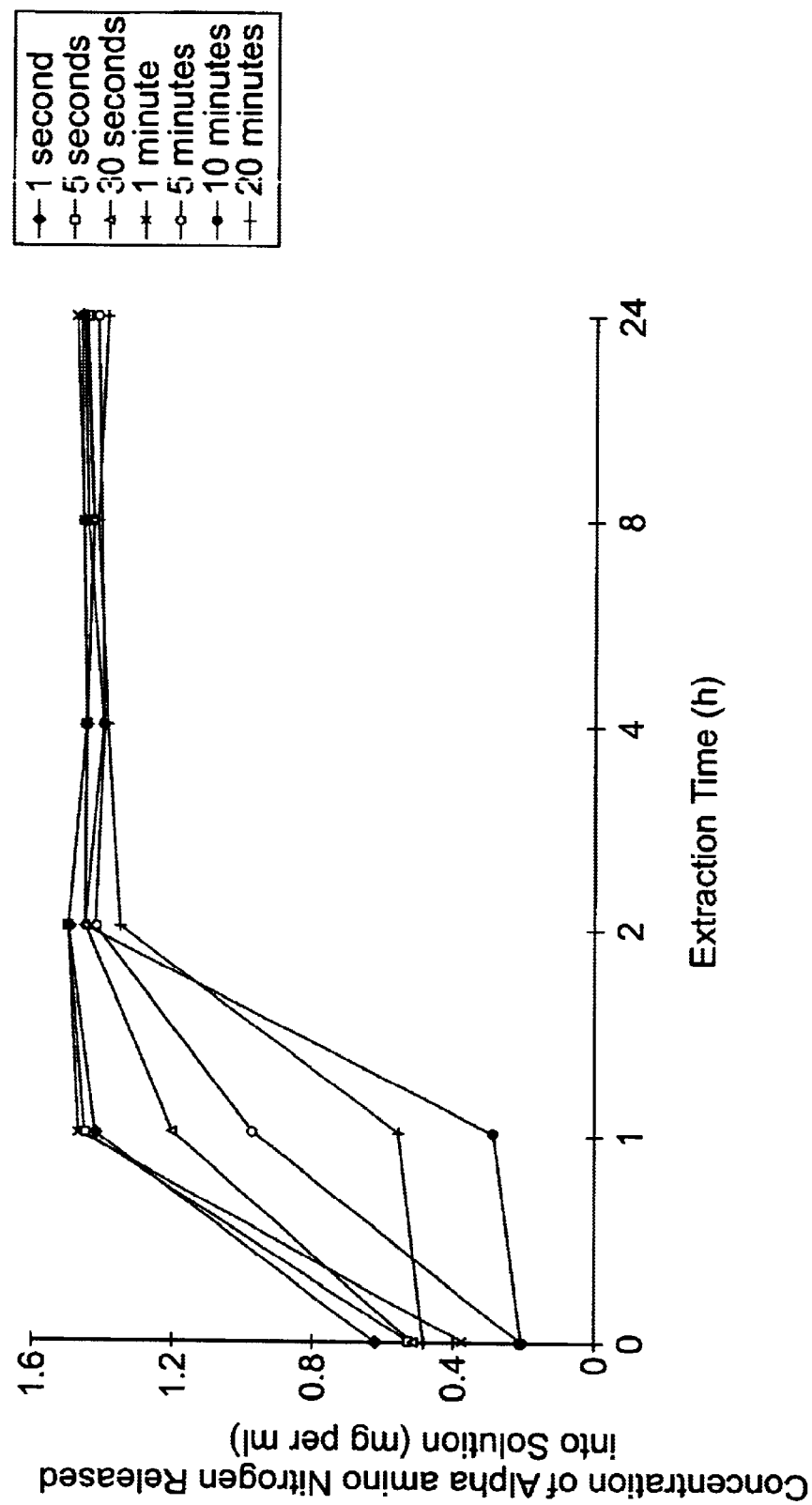

Residency time in the gelling bath did not affect the pattern of release of PKU mixture from the beads in 2M hydrochloric acid (FIG. 14) or in the presence of α-amylase (FIG. 15). The final yields from these modes of extraction were similar (1.35–1.42 mg α-amino N.ml$^{-1}$) for acid extraction, 1.39–1.47 mg α-amino N.ml$^{-1}$, for α-amylase treatment), but much greater than those obtained for from aqueous extraction of the same samples (FIG. 13). This is illustrated for one sample (80% alginic acid:20% starch) in FIG. 16, with the final yield of aqueous extraction being considerably less (0.55 mg α-amino N.ml$^{-1}$) than that obtained using the other extraction methods (1.35 to 1.39 mg α-amino N.ml$^{-1}$).

Conclusions

The alginic acid:starch composition of beads influenced the amount of glycine extracted from them in deionised water at 37° C. Beads containing 40 to 80% alginic acid gave higher yields of extracted glycine than those containing 20% and 100%. This means that beads can be made using 50% starch, which might be desirable in the context of the better enzyme digestibility and safety of starch, relative to alginic acid. It took longer to achieve maximum extraction from samples containing 100% alginic acid than for other formulations.

The botanical source of the starch used to make the beads influenced the pattern of glycine release from beads extracted with deionised water. The lowest final yields of extracted were obtained in beads where fructose was used, whilst the highest were obtained when maize was employed.

The release of glycine from beads suspended in deionised water was not affected by changes in the $CaCl_2$ concentration in the gelling bath used to make them, with beads yielding the same amount of amino acid regardless of the $CaCl_2$ concentration used.

For oven temperatures up to 50° C., the rate of moisture loss from the beads during drying increased with drying temperature. Samples dried at temperatures of 50° C. and higher had similar rates of moisture loss.

Alginic acid:starch ratio had no effect on the amount of glycine released from beads extracted with 2M HCl. Acid extraction and α-amylase digestion gave similar final yields of extract, which were higher than those obtained using aqueous extraction.

Omission of glycine as a component of the gelling bath produced beads giving lower yields of extracted PKU amino acid mixture on extraction in deionised water than was the case for beads extracted in hydrochloric acid or α-amylase.

The time that beads were left in the gelling bath before being removed for drying had no effect on the release of glycine from the beads in any of the extraction systems tested.

What is claimed is:

1. A solid, erodible composition for oral administration comprising an active material and a divalent or multivalent cation cross-linked polysaccharide, the active material being uniformly distributed throughout said composition wherein the composition further comprises an amorphous, gelatinised or pre-gelatinised digestible polymer, the polysaccharide and digestible polymer together forming an interpenetrating polymeric matrix which forms a gel in the presence of a divalent or multivalent cation to form a cation cross-linked polymer matrix, wherein said active material is entangled in the polymeric matrix, wherein the digestible polymer is selected from the group consisting of starch, starch derivatives and α-glucans.

2. A composition according to claim 1, in which the polysaccharide is selected from the group consisting of alginic acid, partially demethylated pectin and demethylated pectin.

3. A composition according to claim 1, in which the source of divalent or multivalent cations is selected from the group consisting of salts of calcium, zinc, copper and iron.

4. A composition according to claim 1, comprising 20 to 60% by weight of the matrix of polysaccharide cross-linked by divalent or multivalent physiologically acceptable metal cations and 80 to 40% by weight of an active ingredient uniformly distributed therein.

5. A method of forming a solid, erodible composition for oral administration comprising an active material and a divalent or multivalent cation cross-linked polysaccharide, the active material being uniformly distributed throughout said composition wherein the composition further comprises an amorphous, gelatinised or pre-gelatinised digestible polymer, the polysaccharide and digestible polymer together forming an interpenetrating polymeric matrix which forms a gel in the presence of a divalent or multivalent cation to form a cation cross-linked polymer matrix, wherein said active material is entangled in the polymeric matrix and wherein the digestible polymer is selected from the group consisting of starch, starch derivatives and α-glucans, said method comprising the steps of forming a solution of polysaccharide saturated with respect to the active material; intimately mixing a sufficient amount of the polysaccharide solution with an active material to form a paste; dispersing the paste in the polysaccharide solution to form a homogeneous dispersion and mixing the homogeneous dispersion with a source of divalent or multivalent cations to form a gel, the method further comprising forming a solution of the digestible polymer, intimately mixing the solution so formed with the polysaccharide solution either before or after the formation of the paste.

6. A method according to claim 5, in which the source of multivalent or divalent cations is in the form of a solution selected from the group consisting of salts of calcium, zinc, copper and iron.

7. A method according to claim 5, in which the polysaccharide solution or solution of polysaccharide and digestible polymer is further saturated with respect to the active material.

8. A method according to claim 7, in which the source of multivalent or divalent cations is further saturated with respect to the active material.

9. A method according to claim 5, in which the homogeneous dispersion is extruded into an aqueous solution of divalent or multivalent cations.

10. A composition according to claim 1, for use in therapy.

11. A medicament comprising a composition according to claim 1, for use in therapy.

12. A kit comprising (i) a paste formed from a solution of polysaccharide and an active material, (ii) a solution of polysaccharide, (iii) an amorphous, gelatinised or pregelatinised digestible polymer selected from the group consisting of starch, starch derivatives and α-glucan and (iv) a source of divalent or multivalent cations.

13. A kit according to claim 12, which further comprises a container, which includes the source of divalent or multivalent cations such that when the paste and polysaccharide solution are mixed together in the container, the cations present therein diffuse into the homogeneous dispersion so formed causing it to gel and entangle the active material into the polymer network so formed.

* * * * *

UNITED STATES PATENT AND TRADEMARK OFFICE
CERTIFICATE OF CORRECTION

PATENT NO.     : 6,649,191 B1
DATED          : October 20, 2000
INVENTOR(S)    : Richard Frank Tester et al.

Page 1 of 1

It is certified that error appears in the above-identified patent and that said Letters Patent is hereby corrected as shown below:

Title page,
Item [73], change "Glasglow" to -- Glasgow --.
Item [30], Foreign Application Priority Data, change "April 20, 1998" to
-- April 22, 1998 --; change "May 15, 1998" to -- May 14, 1998 --; and change
"9806595" to -- 9808595 --.

Signed and Sealed this

Twenty-fifth Day of May, 2004

JON W. DUDAS
*Acting Director of the United States Patent and Trademark Office*